(12) United States Patent
Deban et al.

(10) Patent No.: US 12,214,001 B2
(45) Date of Patent: *Feb. 4, 2025

(54) CANCER THERAPY

(71) Applicant: PROKARIUM LIMITED, London (GB)

(72) Inventors: Livija Deban, London (GB); Hyam Levitsky, Seattle, WA (US)

(73) Assignee: Prokarium Limited, London (GB)

( * ) Notice: Subject to any disclaimer, the term of this patent is extended or adjusted under 35 U.S.C. 154(b) by 92 days.

This patent is subject to a terminal disclaimer.

(21) Appl. No.: 18/076,133

(22) Filed: Dec. 6, 2022

(65) Prior Publication Data
US 2023/0143897 A1    May 11, 2023

Related U.S. Application Data

(63) Continuation of application No. 17/344,065, filed on Jun. 10, 2021, now Pat. No. 11,529,378.

(60) Provisional application No. 63/037,179, filed on Jun. 10, 2020.

(30) Foreign Application Priority Data

Jul. 8, 2020 (EP) .................... 20184698

(51) Int. Cl.
*A61K 35/74* (2015.01)
*A61K 39/00* (2006.01)
*A61K 45/06* (2006.01)
*A61P 35/00* (2006.01)
*A61K 9/00* (2006.01)

(52) U.S. Cl.
CPC .......... *A61K 35/74* (2013.01); *A61K 39/4611* (2023.05); *A61K 39/4631* (2023.05); *A61K 39/4644* (2023.05); *A61K 45/06* (2013.01); *A61P 35/00* (2018.01); *A61K 9/0053* (2013.01)

(58) Field of Classification Search
CPC .................................................... A61K 35/74
See application file for complete search history.

(56) References Cited

U.S. PATENT DOCUMENTS

| | | | |
|---|---|---|---|
| 8,647,618 B2 | 2/2014 | Leonard et al. | |
| 11,529,378 B2 * | 12/2022 | Deban | A61P 37/02 |
| 2020/0071702 A1 | 3/2020 | Thanos et al. | |

FOREIGN PATENT DOCUMENTS

| | | |
|---|---|---|
| EP | 2801364 A1 | 11/2014 |
| WO | 2016/011362 A1 | 1/2016 |
| WO | 2018/083209 A1 | 5/2018 |
| WO | 2018/106754 A1 | 6/2018 |
| WO | 2020/097424 A1 | 11/2019 |
| WO | 2020/176764 A1 | 9/2020 |
| WO | 2021/071468 A1 | 4/2021 |

OTHER PUBLICATIONS

Almasbak et al., "CAR T Cell Therapy: A Game Changer in Cancer Treatment," J. of Immunol. Res., 4(5):467-10, Jan. 2016.
Binder et al., Oncoimmunology, vol. 5, No. 6, pp. 1-7, 2016.
Gharbavi et al., "A recently developed approach in tumor therapy using *Salmonella*," Biotechnolgia (Poznan), 101(3):253-267, 2020.
Wang et al., "Systemic administration of attenuated *Salmonella typhimurium* in combination with interleukin-21 for cancer theapy," Mol. and Clin. Oncol., 1:461-465, 2013.
Extended European Search Report, EP Appl. 20184698.7, European Patent Office, Dec. 21, 2020.

* cited by examiner

*Primary Examiner* — Albert M Navarro
(74) *Attorney, Agent, or Firm* — Gavrilovich, Dodd & Lindsey LLP

(57) ABSTRACT

The present invention relates to the field of cancer therapy. In particular, the present invention relates to a live attenuated Gram-negative bacterium for use in the treatment, reduction, inhibition or control of a neoplastic disease in a subject undergoing or intended to undergo immunotherapy with a checkpoint inhibitor therapy, an adoptive T cell therapy and/or an allogeneic or an autologous CAR-T therapy simultaneously, separately or sequentially with the administration of the live attenuated Gram-negative bacterium.

20 Claims, 13 Drawing Sheets

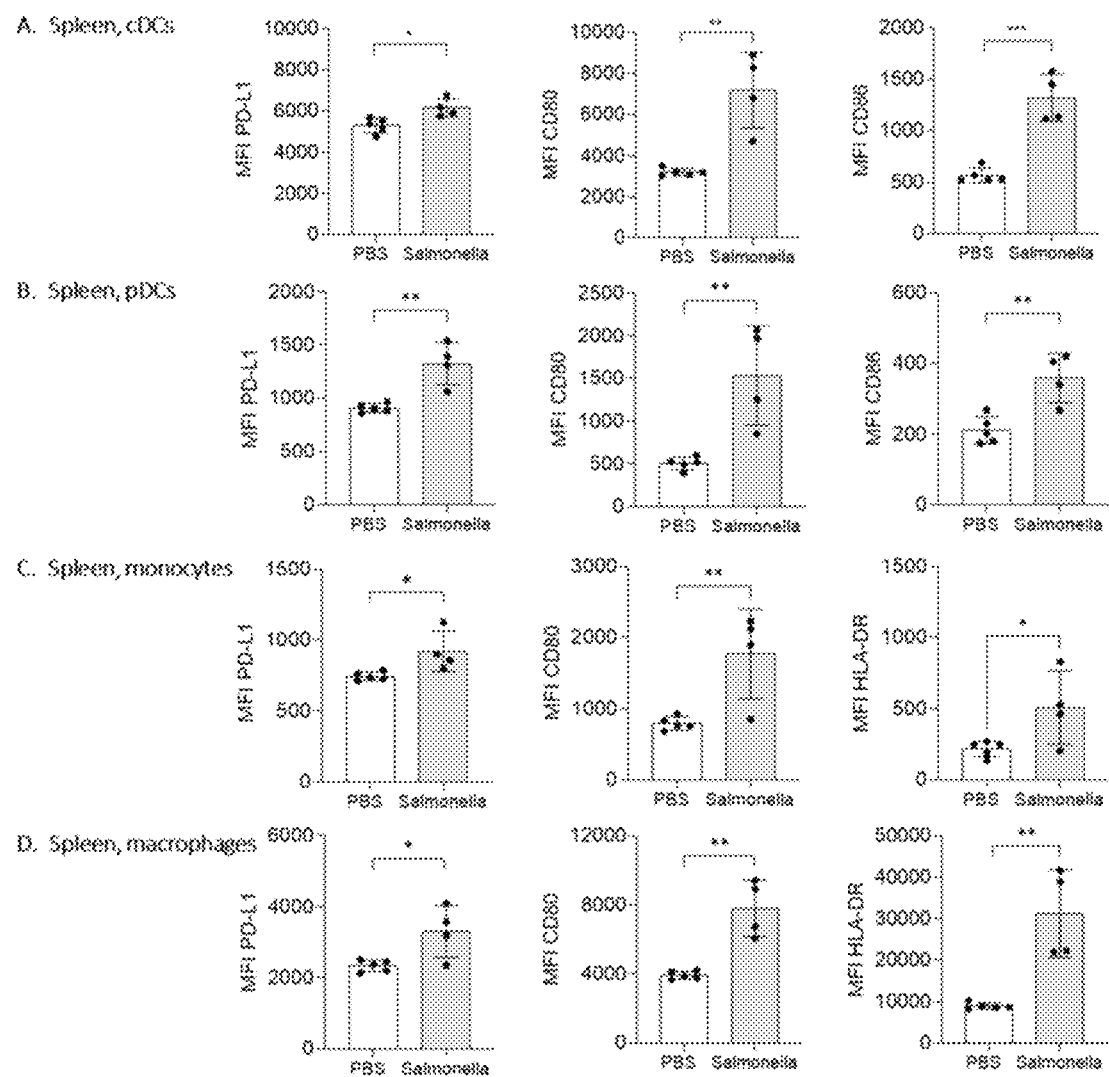
FIGURE 1A-D

CANCER THERAPY

CROSS REFERENCE TO RELATED APPLICATIONS

This application is a continuation of U.S. application Ser. No. 17/344,065, filed Jun. 10, 2021, which application claims priority under 35 U.S.C. § 119 from Provisional Application Ser. No. 63/037,179, filed Jun. 10, 2020, and from European Application No. 20184698.7, filed Jul. 8, 2020, the disclosures of which are incorporated herein by reference.

FIELD OF THE INVENTION

The present invention relates to the field of cancer therapy. In particular, the present invention relates to a method of preventing, treating or inhibiting the development of neoplastic disease in a subject.

BACKGROUND

The field of cancer therapy is continually evolving with new therapies as our understanding of the underlying mechanisms associated with cancer formation and progression improve.

One of the most promising therapeutic strategies for cancer patients at present is that of immunotherapy. This kind of therapy is directed at boosting the body's natural defences in order to fight the cancer or tumour. It capitalises on the substances made by the body, or artificially in a laboratory, to improve or restore immune system function. Types of immunotherapy include monoclonal antibodies, tumour-agnostic therapies, non-specific immunotherapies, oncolytic virus therapy, adoptive cell transfer e.g. CAR T-cell therapy and cancer vaccines. Non-specific immunotherapies include treatment with interferons or interleukins, molecules which help the immune system fight cancer and either slow the growth of cancer cells or, in some instance, destroy the cancer. Immunotherapies may be given instead of traditional cancer treatments, such as chemotherapy or radiation therapy, or in combination with such treatments.

Whilst immunotherapies are successful to a degree, there still remains substantial challenges to overcome. One such issue is the resulting side effects of immunotherapies. The purpose of immunotherapies is to spur the immune system into action and as a result make the cancer or tumour more vulnerable to patrolling immune cells. However, by blocking control mechanisms of the immune activation, some immunotherapies result in side effects due to autoimmune toxicities. Additionally, some immunotherapies are unable to distinguish between cancerous and healthy cells. As a result, the quality of a life of an individual may be seriously impacted.

Additionally, whilst immunotherapy has been shown to be effective, there are still a large proportion of individuals that remain refractory to cancer treatment. There are a number of reasons why such therapies may not be as efficacious as first expected in some individuals. These include the complexity of the cancer to be treated, the health of the individual undergoing treatment (older individuals and individuals with underlying health conditions are known to have weaker immune systems), the ability of cancer cells to 'hide' from the immune system and the challenge of cancer cells having the ability to dampen the response of the immune system.

Accordingly, there remains a significant need in the cancer field for methods that can improve the toxicity profile of currently used immunotherapies, whilst maintaining the efficacy of said treatment in those individuals who respond positively. At the same time, there is a significant need for methods that can improve the efficacy of immunotherapy treatments in individuals who otherwise would be refractory to said treatment.

SUMMARY OF THE INVENTION

The present invention provides an effective method for treating and/or preventing neoplastic disease in a subject by administering a live attenuated Gram-negative bacterium in combination with a checkpoint inhibitor therapy, an adoptive cell therapy and/or an allogeneic or an autologous CAR T-cell therapy. The inventors have surprisingly found that this combination results in a more efficacious therapy than if the subject was treated with either element alone i.e. an additive or synergistic effect is achieved. It is believed that the systemic modifications observed from administering the live attenuated Gram-negative bacteria, in combination with the intestinal uptake of said live attenuated Gram-negative bacteria, can enhance anti-tumour activity of cancer immunotherapies.

In a first aspect of the invention, there is a live attenuated Gram-negative bacterium for use in the treatment, reduction, inhibition or control of a neoplastic disease in a subject undergoing or intended to undergo a checkpoint inhibitor therapy, an adoptive cell therapy and/or an allogeneic or an autologous CAR-T therapy, simultaneously, separately or sequentially with the administration of the live attenuated Gram-negative bacterium, wherein the live attenuated Gram-negative bacterium is orally administered, subcutaneously administered or intramuscularly administered.

In a second aspect of the invention, there is a live attenuated Gram-negative bacterium for use in the treatment, reduction, inhibition or control of a neoplastic disease in a subject undergoing or intended to undergo a checkpoint inhibitor therapy, an adoptive cell therapy and/or an allogeneic or an autologous CAR-T therapy, wherein the live attenuated Gram-negative bacterium is to be administered in a first treatment phase and the checkpoint inhibitor therapy, the adoptive T cell therapy and/or an allogeneic or an autologous CAR-T therapy is to be administered in a second treatment phase.

In a third aspect of the invention, there is a live attenuated Gram-negative bacterium for use in the treatment, reduction, inhibition or control of a neoplastic disease in a subject undergoing or intended to undergo a checkpoint inhibitor therapy, an adoptive cell therapy and/or an allogeneic or an autologous CAR-T therapy simultaneously, separately or sequentially with the administration of the live attenuated Gram-negative bacterium, wherein said live attenuated Gram-negative bacterium is non-recombinant or wherein said live attenuated Gram-negative bacterium does not comprise eukaryotic heterologous DNA encoding a therapeutic protein.

In a fourth aspect of the invention, there is a method of treating, inhibiting or controlling a neoplastic disease in a subject, wherein the method comprises simultaneously, separately or sequentially administering to the subject, (i) a live attenuated Gram-negative bacterium, wherein said live attenuated Gram-negative bacterium is orally administered, subcutaneously administered or intramuscularly administered and (ii) a checkpoint inhibitor therapy, an adoptive cell therapy and/or an allogeneic or an autologous CAR-T therapy, wherein said method results in an enhanced therapeutic efficacy relative to the administration of the live attenuated Gram-negative bacterium or checkpoint inhibitor therapy, an adoptive cell therapy and/or an allogeneic or an autologous CAR-T therapy alone.

In a fifth aspect of the invention, there is a method of treating, inhibiting or controlling a neoplastic disease in a subject, wherein the method comprises simultaneously, separately or sequentially administering to the subject, (i) a live attenuated Gram-negative bacterium, wherein the live attenuated Gram-negative bacterium is to be administered in a first treatment phase and (ii) a checkpoint inhibitor therapy, an adoptive cell therapy and/or an allogeneic or an autologous CAR-T therapy is to be administered in a second treatment phase, wherein said method results in an enhanced therapeutic efficacy relative to the administration of the live attenuated Gram-negative bacterium or checkpoint inhibitor therapy, an adoptive cell therapy and/or an allogeneic or an autologous CAR-T therapy alone.

In a sixth aspect of the invention, there is a method of treating, inhibiting or controlling a neoplastic disease in a subject, wherein the method comprises simultaneously, separately or sequentially administering to the subject, (i) a live attenuated Gram-negative bacterium, wherein said live attenuated Gram-negative bacterium is non-recombinant, or wherein said live attenuated Gram-negative bacterium does not comprise eukaryotic heterologous DNA encoding a therapeutic protein, and (ii) a checkpoint inhibitor therapy, an adoptive cell therapy and/or an allogeneic or an autologous CAR-T therapy, wherein said method results in an enhanced therapeutic efficacy relative to the administration of the live attenuated Gram-negative bacterium or checkpoint inhibitor therapy, an adoptive cell therapy and/or an allogeneic or an autologous CAR-T therapy alone.

DESCRIPTION OF FIGURES

FIG. 1A-D shows orally administered *Salmonella* induces significant changes in the long-term phenotype of systemic myeloid cells. A&B) Graphs show median fluorescence intensity of markers CD80, CD86 and PD-L1 on viable, $CD11c^{high}$, $HLA-DR^+$, $CD11b^{+/-}$, $PDCA-1^-$ conventional dendritic cells and viable, $CD11c^{-/low}$, $PDCA1^+$, $HLA-DR^{-/int}$, $CD11b^-$ plasmacytoid dendritic cells; C&D) Graphs show median fluorescence intensity of markers PD-L1, CD80 and HLA-DR on viable, $CD11c^-$, $CD11b^+$, $Ly6C^+$, $F4/80^-$ monocytes and viable, $CD11c^-$, $CD11b^+$, $Ly6C^-$, $F4/80^+$ macrophages. n=4 or 5 mice/group.

DETAILED DESCRIPTION

Figure 2A:
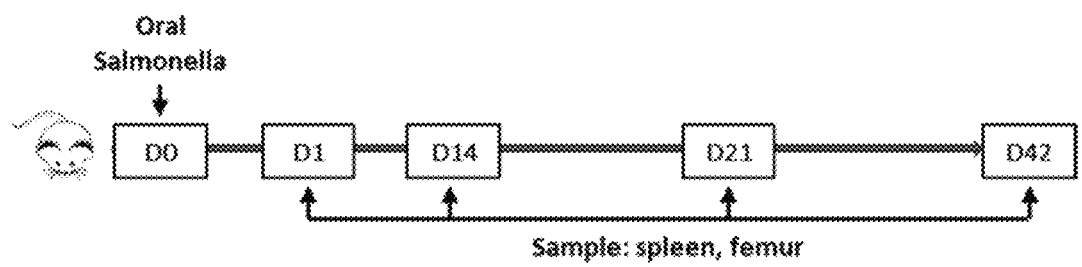
FIG. 2A-C shows a time-course of *Salmonella*-induced phenotypic changes. A) Experiment schematic detailing the timeline of experiments; B) Graphs show median fluorescence intensity of markers CD80 and CD86 as a percentage of the PBS control group mean for viable, $CD11c^{high}$, $HLA-DR^+$, $CD11b^{+/-}$, $PDCA-1^-$ conventional dendritic cells (cDC), and viable, $CD11c^{-/low}$, $PDCA1^+$, $HLA-DR^{-/int}$, $CD11b^-$ plasmacytoid dendritic cells (pDC). Shown are means of n=4-5 mice/group; C) Graphs show median fluorescence intensity of markers CD80, PD-L1 and HLA-DR as a percentage the PBS control group mean for; viable, $CD11c^-$, $CD11b^+$, $Ly6C^+$, $F4/80^-$ monocytes, and $CD11c^-$, $CD11b^+$, $Ly6C^-$, $F4/80^+$ macrophages. Shown are means of n=4-5 mice/group.

In order that the present invention may be more readily understood, certain terms are first defined. Additional definitions are set forth throughout the detailed description.

As used herein, the term "attenuated" refers to a bacterium that has been genetically modified so as not to cause illness in a human or animal subject/model.

By "immunotherapy", we refer to particular therapies aimed at modulating immune system components, such as antibodies or immunocytes, or by drugs or other agents that stimulate, inhibit or otherwise modulate the immune system. In the context of the present invention, the term "immunotherapy" refers to checkpoint inhibitor therapy, adoptive cell therapy and/or autologous or allogeneic CAR T-cell therapy.

By "cellular components of the immune system", we refer to immunocytes such as lymphocytes, such as T and B lymphocytes, gamma-delta T-cells, and NK cells, which may recognize specific antigens, such as prion, viral, bacterial, yeast, fungal, parasite, tumor-associated or tumor-specific antigens, or other antigens associated with a particular disease, disorder or condition. Other immunocytes we refer to include white blood cells, which may be granulocytes or agranulocytes. Examples of immunocytes include neutrophils, eosinophils, basophils, lymphocytes, monocytes and macrophages. Dendritic cells, microglia, and other antigen-presenting cells are also included within this definition.

By "immunotherapeutic composition", we refer to any composition comprising an immunotherapeutic agent. Examples may be pharmaceutically acceptable carriers, biological response modifiers to enhance the immune response and/or adjuvants/excipients or diluents.

As used herein, the term "attenuated" in the context of the present invention, refers to the alteration of a microorganism to reduce its pathogenicity, rendering it harmless to the host, whilst maintaining its viability. This method is commonly used in the development of vaccines due to its ability to elicit a highly specific immune response whilst maintaining an acceptable safety profile. Development of such vaccines may involve a number of methods, examples include, but are not limited to, passing the pathogens under in vitro conditions until virulence is lost, chemical mutagenesis and genetic engineering techniques. Such an attenuated microorganism is preferably a live attenuated microorganism, although non-live attenuated microorganisms are also disclosed.

By "non-natural bacterium or bacteria" we mean a bacterial (prokaryotic) cell that has been genetically modified or "engineered" such that it is altered with respect to the naturally occurring cell. Such genetic modification may for example be the incorporation of additional genetic information into the cell, modification of existing genetic information or indeed deletion of existing genetic information. This may be achieved, for example, by way of transfection of a recombinant plasmid into the cell or modifications on directly to the bacterial genome.

By "inactivating mutations", we mean modifications of the natural genetic code of a particular gene or gene promoter associated with that gene, such as modification by changing the nucleotide code or deleting sections of nucleotide or adding non-coding nucleotides or non-natural nucleotides, such that the particular gene is either not transcribed or translated appropriately or is expressed into a non-active protein such that the gene's natural function is abolished or reduced to such an extent that it is not measurable. Thus, the mutation of the gene inactivates that gene's function or the function of the protein which that gene encodes.

The terms "tumour," "cancer" and "neoplasia" are used interchangeably and refer to a cell or population of cells whose growth, proliferation or survival is greater than growth, proliferation or survival of a normal counterpart cell, e.g. a cell proliferative or differentiative disorder. Typically, the growth is uncontrolled. The term "malignancy" refers to invasion of nearby tissue. The term "metastasis" refers to spread or dissemination of a tumour, cancer or neoplasia to other sites, locations or regions within the subject, in which the sites, locations or regions are distinct from the primary tumour or cancer.

A "checkpoint inhibitor" is an agent, which acts on surface proteins considered checkpoints of the immune response, which are members of either the TNF receptor or B7 superfamilies, or others, including agents which bind to negative costimulatory molecules. Examples of such checkpoint inhibitors include, but are not limited to, agents binding to CTLA-4, PD-1, TIM-3, BTLA, TIGIT, VISTA, LAG-3, and/or their respective ligands, including PD-L1. In the context of the present invention, the term "agent" may refer to an antibody, a small molecule, an antibody fragment or any other binding and/or blocking agent.

The terms "Programmed Death 1," "Programmed Cell Death 1," "Protein PD-1," "PD-1", CD279 and "PD1," are used interchangeably, and include variants, isoforms, species homologs of human PD-1, and analogs having at least one common epitope with PD-1. The complete PD-1 sequence can be found under GenBank Accession No. NP_005009.2.

The terms "PD-L1", "PDL1", "programmed death ligand 1", CD274 and "programmed cell death 1" are used interchangeably and taken to include variants, isoforms and species homologs of human PD-L1, and analogs having at least one common epitope with PD-L1. The complete PD-L1 sequence can be found under GenBank Accession No. NP_054862.1.

The terms "cytotoxic T lymphocyte-associated antigen-4," "CTLA-4," "CTLA4," CD152 and "CTLA-4 antigen" are used interchangeably, and include variants, isoforms, species homologs of human CTLA-4, and analogs having at least one common epitope with CTLA-4. The complete CTLA-4 sequence can be found under GenBank Accession No. NP_005205.2.

The terms "LAG-3", "LAG3", CD223 and "lymphocyte-activation gene 3" are used interchangeably and taken to include variants, isoforms and species homologs of human LAG-3, and analogs having at least one common epitope with LAG-3. The complete LAG-3 sequence can be found under GenBank Accession No. NP_002277.4.

The terms "TIM-3", "TIM3", "HAVCR2", "hepatitis A virus cellular receptor 2", CD366 and "T-cell immunoglobulin domain and mucin domain 3" are used interchangeably and taken to include variants, isoforms and species homologs of human TIM-3, and analogs having at least one common epitope with TIM-3. The complete TIM-3 sequence can be found under GenBank Accession No. NP_116171.3.

The terms "BTLA", "B and T lymphocyte attenuator" and "CD272" are used interchangeably and taken to include variants, isoforms and species homologs of human BTLA, and analogs having at least one common epitope with BTLA. The complete BTLA sequence can be found under GenBank Accession No. NP_861445.4.

The terms "VISTA", "V-set immunoregulatory receptor", "B7H5", "B7-H5", "PD-1H" and "V-domain Ig suppressor of T cell activation" are used interchangeably and taken to include variants, isoforms and species homologs of human VISTA, and analogs having at least one common epitope with VISTA. The complete VISTA sequence can be found under GenBank Accession No. NP_071436.1.

The terms "TIGIT", "T cell immunoreceptor with Ig and ITIM domains", "WUCAM" and "Vstm3" are used interchangeably and taken to include variants, isoforms and species homologs of human TIGIT and analogs having at least one common epitope with TIGIT. The complete TIGIT sequence can be found under GenBank Accession No. NP_776160.2.

The term "therapeutic antibody" as referred to herein includes whole antibodies and any antigen-binding fragment (i.e., "antigen-binding portion") or single chains thereof which results in a therapeutic effect.

Such therapeutic antibodies may be directed at the checkpoint inhibitor molecules directed above or include agonistic antibodies directed at co-stimulatory molecule targets such as ICOS (inducible T-cell costimulatory/CD278), GITR (glucocorticoid-induced TNF receptor/TNFRSF18/CD357/AITR), 4-1 BB (CD137), CD27 and CD40. In some instances, it may be desirable for the subject to receive both types of therapeutic antibody.

The term "monoclonal antibody" as used herein refer to a preparation of antibody molecules of single molecular composition. A monoclonal antibody composition displays a single binding specificity and affinity for a particular epitope. The monoclonal antibody may be a human antibody or a humanised antibody.

The term "adoptive cell therapy" is intended to refer to any therapy that involves the transfer/administration of cells into a subject, preferably a human. The cells may be autologous or allogeneic. Preferably, the cells are commonly derived from the immune system with the goal of improving immune functionality. Adoptive cell therapy may include, but is not limited to, CAR T-cell therapy (chimeric antigen receptor T-cell), TIL therapy (tumour infiltrating lymphocytes), TCR therapy) engineered T-cell receptor therapy, NK therapy (natural killer cells) and/or iPSC-derived therapy (induced pluripotent stem cells).

The terms "effective amount" or "pharmaceutically effective amount" refer to a sufficient amount of an agent to provide the desired biological or therapeutic result. That result can be reduction, amelioration, palliation, lessening, delaying, and/or alleviation of one or more of the signs, symptoms, or causes of a disease, or any other desired alteration of a biological system. In reference to cancer, an effective amount may comprise an amount sufficient to cause a tumour to shrink and/or to decrease the growth rate of the tumour (such as to suppress tumour growth) or to prevent or delay other unwanted cell proliferation. In some embodiments, an effective amount is an amount sufficient to delay development, or prolong survival or induce stabilisation of the cancer or tumour.

In some embodiments, a therapeutically effective amount is an amount sufficient to prevent or delay recurrence. A therapeutically effective amount can be administered in one or more administrations. The therapeutically effective amount of the drug or combination may result in one or more of the following: (i) reduce the number of cancer cells; (ii) reduce tumour size; (iii) inhibit, retard, slow to some extent and preferably stop cancer cell infiltration into peripheral organs; (iv) inhibit (i.e., slow to some extent and preferably stop) tumour metastasis; (v) inhibit tumour growth; (vi) prevent or delay occurrence and/or recurrence of tumour; and/or (vii) relieve to some extent one or more of the symptoms associated with the cancer.

For example, for the treatment of tumours, a "therapeutically effective dosage" may induce tumour shrinkage by at least about 5% relative to baseline measurement, such as at least about 10%, or about 20%, or about 60% or more. The baseline measurement may be derived from untreated subjects.

A therapeutically effective amount of a therapeutic compound can decrease tumour size, or otherwise ameliorate symptoms in a subject. One of ordinary skill in the art would be able to determine such amounts based on such factors as the subject's size, the severity of the subject's symptoms, and the particular composition or route of administration selected.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells.

The term "treatment" or "therapy" refers to administering an active agent with the purpose to cure, heal, alleviate, relieve, alter, remedy, ameliorate, improve, or affect a condition (e.g., a disease), the symptoms of the condition, or to prevent or delay the onset of the symptoms, complications, biochemical indicia of a disease, or otherwise arrest or inhibit further development of the disease, condition, or disorder in a statistically significant manner.

As used herein, the term "subject" is intended to include human and non-human animals. Preferred subjects include human patients in need of enhancement of an immune response. The methods are particularly suitable for treating human patients having a disorder that can be treated by augmenting the immune response. In a particular embodiment, the methods are particularly suitable for treatment of cancer in vivo.

"Simultaneous" administration, as defined herein, includes the administration of the live attenuated bacterium and immunotherapeutic composition within about 2 hours or about 1 hour or less of each other, even more preferably at the same time.

"Separate" administration, as defined herein, includes the administration of the live attenuated bacterium and immunotherapeutic composition, more than about 12 hours, or about 8 hours, or about 6 hours or about 4 hours or about 2 hours apart.

"Sequential" administration, as defined herein, includes the administration of the live attenuated bacterium and immunotherapeutic composition each in multiple aliquots and/or doses and/or on separate occasions. The immunotherapeutic composition may be administered to the patient before and/or after administration of the live attenuated bacterium. Alternatively, the immunotherapeutic composition is continued to be applied to the patient after treatment with the live attenuated bacterium.

The use of the alternative (e.g., "or") should be understood to mean either one, both, or any combination thereof of the alternatives. As used herein, the indefinite articles "a" or "an" should be understood to refer to "one or more" of any recited or enumerated component.

As used herein, "about" means within an acceptable error range for the particular value as determined by one of ordinary skill in the art, which will depend in part on how the value is measured or determined, i.e., the limitations of the measurement system. For example, "about" can mean within 1 or more than 1 standard deviation per the practice in the art. Alternatively, "about" can mean a range of up to 20%. When particular values are provided in the application and claims, unless otherwise stated, the meaning of "about" should be assumed to be within an acceptable error range for that particular value.

As used herein, the terms "non-recombinant" and "non-recombinant strain(s)" are used interchangeably and in the context of the present invention refers to the fact that these strains do not contain genes or gene fragments from eukaryotic organisms. As such, the strains herein disclosed do not act as "carrier strains" for the purpose of delivering therapeutic molecules to a subject/patient. Accordingly, the strains herein disclosed do not encode eukaryotic heterologous DNA, or eukaryotic heterologous DNA that encodes a therapeutic molecule, or eukaryotic DNA that encodes for proteins, or fragments thereof, that are intended as antigens.

As used herein, the terms "systemic" and "systemically activated" are used interchangeably and in the context of the present invention refers to a widespread immune response throughout the body of a subject, as opposed to a local, spatially-restricted response. Preferably, the systemic immune response involves the activation and/or maturation of myeloid cells, for example, dendritic cells, monocytes and/or macrophages and in the context of the present invention is thought to help "condition" the immune system of the subject, such that the subject is more responsive to an immunotherapy, such as a checkpoint inhibitor, an adoptive cell therapy and/or a CAR T-cell therapy. Accordingly, the Gram-negative bacteria may act to "prime", "boost", "amplify", "enhance", "improve", "augment", "pre-activate" or "promote" the immune response of a subject following administration of the second composition. The aforementioned terms are used interchangeably with the term "conditioned".

As used herein, the terms "tumour-agnostic therapy" or "agnostic to tumour type" are used interchangeably and refer to a type of therapy that uses drugs or other substances to treat cancer based on the genetic and/or molecular features without regard to the cancer type or where the cancer started in the body.

In a first aspect of the invention, there is a live attenuated Gram-negative bacterium for use in the treatment, reduction, inhibition or control of a neoplastic disease in a subject undergoing or intended to undergo a checkpoint inhibitor therapy, an adoptive cell therapy and/or an allogeneic or an autologous CAR-T therapy, simultaneously, separately or sequentially with the administration of the live attenuated Gram-negative bacterium, wherein the live attenuated Gram-negative bacterium is orally administered, subcutaneously administered or intramuscularly administered.

In a second aspect of the invention, there is a live attenuated Gram-negative bacterium for use in the treatment, reduction, inhibition or control of a neoplastic disease in a subject undergoing or intended to undergo a checkpoint inhibitor therapy, an adoptive cell therapy and/or an allogeneic or an autologous CAR-T therapy, wherein the live attenuated Gram-negative bacterium is to be administered in a first treatment phase and the checkpoint inhibitor therapy, the adoptive T cell therapy and/or the allogeneic or the autologous CAR-T therapy is to be administered in a second treatment phase.

In a third aspect of the invention, there is a live attenuated Gram-negative bacterium for use in the treatment, reduction, inhibition or control of a neoplastic disease in a subject undergoing or intended to undergo a checkpoint inhibitor therapy, an adoptive cell therapy and/or an allogeneic or an autologous CAR-T therapy simultaneously, separately or sequentially with the administration of the live attenuated Gram-negative bacterium, wherein said live attenuated Gram-negative bacterium is non-recombinant or wherein said live attenuated Gram-negative bacterium does not comprise eukaryotic heterologous DNA encoding a therapeutic protein.

It is envisaged that the live attenuated Gram-negative bacterium may therefore act as a conditioning agent of a subject's immune system, resulting in the subject's immune system being able to mount an effective immune response to a neoplastic disease when treated with the checkpoint inhibitor, adoptive cell therapy and/or an autologous or allogeneic CAR-T therapy.

The live attenuated bacterium of the present invention is a Gram-negative bacterium. Examples of Gram-negative bacteria for use in the present invention include, but are not limited to, *Escherichia coli*, *Salmonella*, *Shigella*, *Pseudomonas*, *Moraxella*, *Helicobacter*, *Stenotrophomonas*, *Bdellovibrio*, *Legionella*, *Chlamydia* and *Yersinia*.

Preferably, the live attenuated Gram-negative bacterium is a *Salmonella* species. Examples of *Salmonella* species for use in the present invention are *Salmonella enterica* and *Salmonella bongori*. *Salmonella enterica* can be further sub-divided into different serotypes or serovars. Examples of said serotypes or serovars for use in the present invention are *Salmonella enterica* Typhi, *Salmonella enterica* Paratyphi A, *Salmonella enterica* Paratyphi B, *Salmonella enterica* Paratyphi C, *Salmonella enterica* Typhimurium and *Salmonella enterica* Enteritidis. In a preferred embodiment, the live attenuated Gram-negative bacterium is *Salmonella enterica* Typhi or *Salmonella enterica* Typhimurium.

In another embodiment of the present invention, the live attenuated gram-negative bacterium is a genetically engineered non-natural bacterium. In a preferred embodiment, the live attenuated Gram-negative bacterium is a non-recombinant bacterium. In another preferred embodiment, the Gram-negative bacterium herein disclosed does not contain genes or gene fragments from eukaryotic organisms.

As would be understood by a person of skill in the art, genes may be mutated by a number of well-known methods in the art, such as homologous recombination with recombinant plasmids targeted to the gene of interest, in which case an engineered gene with homology to the target gene is incorporated into an appropriate nucleic acid vector (such as a plasmid or a bacteriophage), which is transfected into the target cell. The homologous engineered gene is then recombined with the natural gene to either replace or mutate it to achieve the desired inactivating mutation. Such modification may be in the coding part of the gene or any regulatory portions, such as the promoter region. As would be understood by a person of skill in the art, any appropriate genetic modification technique may be used to mutate the genes of interest, such as the CRISPR/Cas system, e.g. CRISPR/Cas9.

Thus, numerous methods and techniques for genetically engineering bacterial strains will be well known to the person skilled in the art. These techniques include those required for introducing heterologous genes into the bacteria either via chromosomal integration or via the introduction of a stable autosomal self-replicating genetic element. Exemplary methods for genetically modifying (also referred to as "transforming" or "engineering") bacterial cells include bacteriophage infection, transduction, conjugation, lipofection or electroporation. A general discussion on these and other methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); which are hereby incorporated by reference.

Accordingly, the present invention discloses a live attenuated bacterium for use, wherein the live attenuated bacterium may be selected from the group comprising Ty21a, CVD 908-htrA, CVD 909, Ty800, M01ZH09, x9633, x9640, x8444, DTY88 ZH9PA, MD58, WTO5, ZH26, SL7838, SL7207, VNP20009 or A1-R. Preferably, the bacteria herein disclosed is a non-recombinant strain, for example, Ty21a, CVD 908-htrA, CVD 909, Ty800, M01ZH09, x9633, x9640, x8444, DTY88, MD58, WTO5, ZH26, SL7838, SL7207, VNP20009 or A1-R. In another embodiment, the bacteria herein disclosed is a strain that has been modified to contain prokaryotic heterologous DNA, for example, ZH9PA. In addition to the aforementioned strains, it is envisaged that any attenuated, non-pathogenic, *Salmonella enterica* serovar *Typhi* or *Typhimurium* strain may be used as herein disclosed, i.e. as a conditioning agent, resulting in a more effective immune response being mounted following immunotherapy administration to a subject.

In one embodiment, the genetically engineered non-natural bacterium may be derived from a *Salmonella* species that may comprise an attenuating mutation in a *Salmonella* Pathogenicity Island 2 (SPI-2) gene and an attenuating mutation in a second gene. Suitable genes and details of such a live attenuated bacterium is as described in WO 2000/68261, which is hereby incorporated by reference in its entirety.

In one embodiment, the SPI-2 gene is an ssa gene. For example, the invention includes an attenuating mutation in one or more of ssaV, ssaJ, ssaU, ssaK, ssaL, ssaM, ssaO, ssaP, ssaQ, ssaR, ssaS, ssaT, ssaD, ssaE, ssaG, ssaI, ssaC and ssaH. Preferably, the attenuating mutation is in the ssaV or ssaJ gene. Even more preferably, the attenuating mutation is in the ssaV gene.

The genetically engineered non-natural bacterium may also comprise an attenuating mutation in a second gene, which may or may not be in the SPI-2 region. The mutation may be outside of the SPI-2 region and involved in the biosynthesis of aromatic compound. For examples, the invention includes an attenuating mutation in an aro gene. In a preferred embodiment, the aro gene is aroA or aroC. Even more preferably, the aro gene is aroC.

The genetically engineered non-natural bacterium may further comprise one or more gene cassettes. Such gene cassettes may be used to deliver additional prokaryotic molecules to support the function of the genetically engineered non-natural bacterium to condition the immune system, or to support the activity of the relevant immunotherapy, i.e. checkpoint inhibitor therapy, adoptive cell therapy and/or CAR T-cell therapy. The skilled person will recognise that the supporting molecule delivered in this manner may be dependent on the immunotherapy to be administered.

In yet another embodiment, the genetically engineered non-natural bacterium may be derived from a *Salmonella* species and may comprise inactivating mutations in one or more genes selected from pltA, pltB, cdtB and ttsA and further comprises attenuating mutations in one or more genes selected from aroA and/or aroC and/or ssaV. Details of said genes and mutations are as described in WO 2019/110819, which is hereby incorporated by reference in its entirety.

It is envisaged that inactivating mutations (e.g. deletions) in the genes pltA, pltB and cdtB will prevent the *Salmonella* species from producing the typhoid toxin and that inactivating mutations (e.g. deletions) in ttsA will prevent the *Salmonella* species from secreting the typhoid toxin. It is envisaged that the non-natural bacterium may be derived from *Salmonella enterica*, in particular.

In an embodiment, the genetically engineered microorganism may be derived from *Salmonella enterica* serovar *Typhi* and comprise a modification in which the lipopolysaccharide O2 O-antigens of *Salmonella enterica* serovar Paratyphi A are expressed. In yet another preferred embodiment, the genetically engineered microorganism is derived from *Salmonella enterica* serovar *Typhi*, wherein said strain comprises a modification in which the flagella proteins of *Salmonella enterica* serovar Paratyphi A are expressed. In some instances, the genetically engineered microorganism may be derived from *Salmonella enterica* serovar *Typhi* and comprise a modification in which both the lipopolysaccharide O2 O-antigens and the flagella proteins of *Salmonella enterica* serovar Paratyphi A are expressed. Details of such modifications can be found in WO2020/157203. Such strains are considered to be non-recombinant in the context of the present invention due to the term "non-recombinant" referring to a bacteria that does not contain eukaryotic genes or gene fragments, or bacteria that acts as a "carrier" strain for the purpose of the delivery of a therapeutic molecules, or delivery of eukaryotic heterologous DNA that encodes for a therapeutic molecule.

Where the methods herein described involve the use of a plasmid, said plasmid will ideally have an origin of replication selected from pMB1, ColE1, p15A, pSC101 and RK2. The plasmid may contain an antibiotic resistance gene selected from β-lactamase (bla), kanamycin phosphotransferase (kan), tetracycline efflux protein (tetA) or chloramphenicol acetyltransferase (cat). Ideally the antibiotic resistance gene will be excised prior to or shortly after transformation into the live bacterial vector strain, for example by a mechanism such as 'X-mark' (Cranenburgh & Leckenby 2012, WO2012/001352). A plasmid maintenance system may be required to prevent plasmid loss. These may include mechanisms to place a native chromosomal gene under a heterologous promoter such as the 'Operator-Repressor Titration for Vaccines' (ORT-VAC; Garmory et al. 2005, Infect. Immun. 73: 2005-2011) or 'oriSELECT' (Cranenburgh 2005, WO 2005/052167) systems, neither of which require an additional selectable marker gene to be present on the plasmid. Alternatively, a selectable marker gene will be used that is not an antibiotic resistance gene, such as a gene to complement a host cell mutation (Degryse 1991, Mol. Gen. Genet. 227: 49-51).

It is envisaged that the present invention may also include the live attenuated strain, according to above, wherein said strain may have its native fliC gene replaced with the fliC gene of *Salmonella enterica* serovar Paratyphi A, such that the conferred serotype is altered from an Hd serotype to a Ha serotype, where 'serotype' refers to a distinct variation within the bacterial species. Details of such a modification can be found in WO2020/157203, which is incorporated herein by reference for all purposes.

An additional embodiment of the present invention is the live attenuated strain described above wherein the strain may be further modified to contain a functional fepE gene, such that long O-antigen chains are generated, preferably wherein the O-antigen chains are 100 repeated units of the trisaccharide backbone in length. Details of such a modification can be found in WO2020/157203.

The fepE gene encodes the length regulator of very long O-antigen chains, wherein 'very long' is taken to mean more than 100 repeated units of the trisaccharide backbone. *Salmonella enterica* serovar *Typhi* does not possess these long O-antigen chains due to a mutation introducing a stop codon into the gene. *Salmonella enterica* serovar *Typhi* may be manipulated into expressing these long O-antigen chains via a number of methods; the natural promoter of fepE may be replaced with an alternative promoter, for example $P_{araBAD}$, the chromosomal mutation of fepE in *Salmonella enterica* serovar *Typhi* may be repaired or a functional copy of fepE may be inserted elsewhere in the *Salmonella enterica* serovar *Typhi* chromosome. An in vivo-induced promoter or a constitutive promoter may be utilised, examples of such promoters include $P_{pagC}$, $P_{nirB}$, $P_{ssaG}$, $P_{sifA}$, $P_{sifB}$, $P_{sseA}$, $P_{sseG}$, $P_{sseJ}$, $P_{lac}$, $P_{tac}$, $P_{trc}$ and lambda $P_L/P_R$. Similar modified sequences may include having at least about 70%, 80%, 85%, 90%, 95%, 96%, 97%, 98% or 99% identity to the wild-type sequence of any of $P_{pagC}$, $P_{nirB}$, $P_{ssaG}$, $P_{sifA}$, $P_{sifB}$, $P_{sseA}$, $P_{sseG}$, $P_{sseJ}$ and lambda $P_L/P_R$.

Preferably, the introduction of these long O-antigen chains may be beneficial in inducing an LPS-specific immune response. There may be an additional benefit where the LPS is naturally very long such as from expression of fepE.

It is further envisaged that the live attenuated strain described above may be modified to constitutively express gtrC or to express gtrC in trans. Details of such a modification can be found in WO2020/157203.

It is further envisaged that the live attenuated strain described above may be further modified to contain an additional copy of the tviA gene under the control of a phagosomally induced promoter. Details of such a modification can be found in WO2020/157203.

The amount of the live attenuated Gram-negative bacterium, whether natural or non-natural, administered to the subject is sufficient to elicit an immune response in the subject, so that the subject's immune system is effectively conditioned to receive a checkpoint inhibitor therapy, an adoptive cell therapy and/or a CAR T-cell therapy, resulting in the subject's immune system being able to mount an effective immune response to the cancer or tumour when treated with said therapies. The immune response initiated by the administration of the live attenuated Gram-negative bacterium may be of a therapeutic level in itself or be of a sub-therapeutic level requiring the administration of the aforementioned immunotherapies to exert a therapeutic effect.

It is envisaged that the live attenuated Gram-negative bacterium may be administered at least once or at least twice, two weeks apart. The live attenuated Gram-negative bacterium may be administered before, during or after checkpoint inhibitor therapy, adoptive cell transfer therapy and/or CAR T-cell therapy. Preferably, at least one administration of the live attenuated Gram-negative bacterium would occur prior to the immunotherapy treatment, such administration may occur at least one week prior to the immunotherapy treatment. It is envisaged that the administration of the live attenuated Gram-negative bacterium may be repeated, depending on the treatment regimen of the immunotherapy. The live attenuated Gram-negative bacterium may be administered at a dose of between $10^5$ and $10^{12}$ CFU, where CFU is a colony-forming unit. For example, suitable doses may be between $10^5$ and $10^6$ CFU, $10^5$ and $10^7$ CFU, $10^5$ and $10^8$ CFU, $10^5$ and $10^9$ CFU, $10^5$ and $10^{10}$ CFU, $10^5$ and $10^{11}$ CFU, $10^6$ and $10^7$ CFU, $10^6$ and $10^8$ CFU, $10^6$ and $10^9$ CFU, $10^6$, and $10^{10}$ CFU, $10^6$ and $10^{11}$ CFU, $10^6$ and $10^{12}$ CFU, $10^7$ and $10^8$ CFU, $10^7$ and $10^9$ CFU, $10^7$ and $10^{10}$ CFU, $10^7$ and $10^{11}$ CFU, $10^7$ and $10^{12}$ CFU, $10^8$ and $10^9$ CFU, $10^8$ and $10^{10}$ CFU, $10^8$ and $10^{11}$ CFU, $10^8$ and $10^{12}$ CFU, $10^9$ and $10^{10}$ CFU, $10^9$ and $10^{11}$ CFU, $10^9$ and $10^{12}$ CFU, $10^{10}$ and $10^{11}$ CFU, $10^{10}$ and $10^{12}$ CFU, or $10^{11}$ and $10^{12}$ CFU.

In one embodiment, the immunotherapy is a checkpoint inhibitor, the term "checkpoint inhibitor" herein refers to a blocking agent directed against a checkpoint molecule. The blocking agent may be an antagonist, an inhibitor or a blocking antibody. Accordingly, the blocking agent may be a small molecule or a biologic drug, in particular instances it is a monoclonal antibody. In a preferred embodiment the checkpoint inhibitor is directed against CTLA-4, PD-1, PD-L1, LAG-3, TIM-3, BTLA, TIGIT, VISTA or any combinations thereof. For example, the checkpoint inhibitor may be directed against PD-1 and PD-L1, PD-1 and CTLA-4, PD-L1 and CTLA-4.

Even more preferably, the checkpoint inhibitor is directed against CTLA-4, PD-1 or PD-L1. In some instances, the blocking agent may be ipilimumab (Yervoy®-targeting CTLA-4), nivolumab (Opdivo®-targeting PD-1), pembrolizumab (Keytruda®-targeting PD-1), atezolizumab (Tecentriq®-targeting PD-L1), cemiplimab (Libtayo®-targeting PD-1) or durvalumab (Imfinzi®-targeting PD-L1).

The PD-L1/PD-1 signalling pathway is a primary mechanism of cancer immune evasion for several reasons. First, and most importantly, this pathway is involved in negative regulation of immune responses of activated T effector cells, found in the periphery. Second, PD-L1 is up-regulated in cancer microenvironments, while PD-1 is also up-regulated on activated tumour infiltrating T cells, thus possibly potentiating a vicious cycle of inhibition. Third, this pathway is intricately involved in both innate and adaptive immune regulation through bi-directional signalling. These factors make the PD-1/PD-L1 complex a central point through which cancer can manipulate immune responses and promote its own progression. As a result, the tumour is able to activate inhibitory immune checkpoint molecule pathways, resulting in a suppressed immune system and the continued unimpeded growth of cancerous cells. Following T-cell activation, CTLA-4 is transported to the surface where it competes with CD28 for the same ligands as on the antigen-presenting cells (APCs), resulting in suppression of CD28 and subsequent suppression of T-cell activation and proliferation. Targeting PD-1, PD-L1 and CTLA-4 aims to prevent these events from occurring.

It is envisaged that the present invention herein disclosed may allow for the conditioning of the innate immune system, thus providing a superior, more complete and/or more durable support for the development, activation and/or maintenance of adaptive anti-tumour responses induced by checkpoint inhibitors.

In one embodiment, the immunotherapy is an adoptive cell therapy, wherein immune cells are transferred into a patient/subject, most commonly due to their improved functionality and characteristics. The cells to be transferred may have originated from the subject (autologous) or from another subject (allogeneic). Examples of such adoptive cell therapies include, but are not limited to engineered or non-engineered macrophages, engineered or non-engineered γδ T cells, engineered or non-engineered natural killer cells. Accordingly, adoptive cell therapies in the context of the present invention include, but are not limited to, tumour-Infiltrating Lymphocyte (TIL) therapy, Engineered T Cell Receptor (TCR) therapy and/or natural killer (NK) cell therapy, the details of which will be well known to those skilled in the art (Adoptive cellular therapies: the current landscape, Rohaan et al. 2019, Virchows Arch. 474(4): 449-461).

In another embodiment, the immunotherapy is a CAR T-cell therapy. The CAR T-cell therapy may be allogeneic or autologous. In some instances, the CAR T-cell therapy will be directed against the antigen CD19, which is present in B-cell derived cancers. Accordingly, such therapy may be particularly suited for B-cell derived cancers, such as acute lymphoblastic leukemia (ALL) and diffuse large B-cell lymphoma (DLBCL). In other instances the CAR T-cell therapy will be directed against tumour-associated antigens (TAAs) and are accordingly more suited for the treatment of solid tumours. Examples of such antigens include, but are not limited to, CD133, CD138, BCMA, CEA, EGFR, EpCAM, GD2, GPC3, HER2, HerinCAR-PD1, MSLN, MG7, MUC1, LMP1, PSMA and PSCA. Such techniques will be known to those skilled in the art and the reader is directed to the review entitled "Adoptive cellular therapies: the current landscape" for further information (Rohaan et al. 2019, Virchows Arch. 474(4): 449-461).

The checkpoint inhibitor may be a therapeutic antibody directed at the cancer or tumour. In particular embodiments, the therapeutic antibody may be a monoclonal antibody, and even more preferred, a humanised or human monoclonal antibody. Methods of obtaining such monoclonal antibodies are known to those skilled in the art. The therapeutic antibody may block an abnormal protein in a cancer cell, attach to specific proteins on cancer cells or be conjugated to a cytotoxic molecules, such as an anticancer drug. The latter flags the cancer cells to the immune system so that the abnormal cells can subsequently be targeted and destroyed by cellular components of the immune system. Examples of monoclonal antibodies that are checkpoint inhibitors include, but are not limited to, ipilimumab (Yervoy®), nivolumab (Opdivo®) and pembrolizumab (Keytruda®).

Due to the multifactorial nature of the cause of disease, it is understood that the immunotherapies herein described, i.e. checkpoint inhibitor therapy, adoptive cell therapy and/or CAR T-cell therapy, may be given in combination to a patient/subject. For example, adoptive cell therapy and checkpoint inhibitors may be used in combination. It is understood that the need for combination therapies will be decided on a case by case basis and be dependent on numerous factors, for example the complexity of the neoplastic disease to be treated and/or the medical history of the patient/subject to be treated.

It is expected that no matter the type of immunotherapy administered to the subject (immunotherapy used may be dependent on form and complexity of the neoplastic disease), the efficacy of said immunotherapy, following the administration of the live attenuated Gram-negative bacterium will be greater than the administration of the immunotherapy component alone. In some instances, the efficacy of the immunotherapy, following the administration of the live attenuated Gram-negative bacterium will be greater than either of the components administered alone. Therefore, the present invention provides for either an additive or a synergistic method of treating a neoplastic disease. It is envisaged that this additive or synergistic effect will be particularly advantageous when treating more complex and/or solid tumours and particularly advantageous for those patients/subjects that are non-responders to treatment with the immunotherapy alone.

The live attenuated Gram-negative bacterium for use in the present invention may be used to treat a neoplastic disease, which is associated with a solid tumour or haematological malignancy. Such diseases include a sarcoma, carcinoma, adenocarcinoma, melanoma, myeloma, blastoma, glioma, lymphoma or leukemia. In a preferred embodiment, the neoplastic disease is associated with a solid tumour. In particular aspects, the neoplastic disease is associated with a cancer selected from prostate cancer, liver cancer, renal cancer, lung cancer, breast cancer, colorectal cancer, bladder cancer, pancreatic cancer, brain cancer, hepatocellular, lymphoma, leukaemia, gastric cancer, cervical cancer, ovarian cancer, thyroid cancer, melanoma, carcinoma, head and neck cancer, skin cancer or sarcoma.

Neoplasia, tumours and cancers include benign, malignant, metastatic and non-metastatic types, and include any stage (I, II, III, IV or V) or grade (G1, G2, G3, etc.) of neoplasia, tumour, or cancer, or a neoplasia, tumour, cancer or metastasis that is progressing, worsening, stabilized or in remission. Cancers that may be treated according to the invention include but are not limited to cells or neoplasms of the bladder, blood, bone, bone marrow, brain, breast, colon, esophagus, gastrointestines, gum, head, kidney, liver, lung, nasopharynx, neck, ovary, prostate, skin, stomach, testis, tongue, or uterus. In addition, the cancer may specifically be of the following histological type, though it is not limited to the following: neoplasm, malignant; carcinoma; undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumour, malignant; bronchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma with squamous metaplasia; thymoma, malignant; ovarian stromal tumour, malignant; thecoma, malignant; granulosa cell tumour, malignant; androblastoma, malignant; Sertoli cell carcinoma; Leydig cell tumour, malignant; lipid cell tumour, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumour; Mullerian mixed tumour; nephroblastoma; hepatoblastoma; carcinosarcoma; mesenchymoma, malignant; Brenner tumour, malignant; phyllodes tumour, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumour of bone; Ewing's sarcoma; odontogenic tumour, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumour; meningioma, malignant; neurofibrosarcoma; neurilemmoma, malignant; granular cell tumour, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Preferably, the neoplastic disease may be tumours associated with a cancer selected from prostate cancer, liver cancer, renal cancer, lung cancer, breast cancer, colorectal cancer, pancreatic cancer, brain cancer, hepatocellular cancer, lymphoma, leukaemia, gastric cancer, cervical cancer, ovarian cancer, thyroid cancer, melanoma, head and neck cancer, skin cancer and soft tissue sarcoma and/or other forms of carcinoma. The tumour may be metastatic or a malignant tumour.

In a preferred embodiment, the neoplastic disease is associated with a cancer selected from lung cancer, renal cancer, bladder cancer, gastric cancer, ovarian cancer, colorectal cancer, melanoma, head and neck cancer or breast cancer.

In a preferred embodiment of the present invention, the live attenuated Gram-negative bacteria is administered orally, subcutaneously or intramuscularly due to these modes of administration being compatible with a systemic activation of the immune system. As used herein, the terms "oral" or "orally administered" are used interchangeably and refer to the Gram-negative bacteria being administered via the mouth of a patient/subject. The terms "subcutaneous" or "subcutaneously administered" are used interchangeably and refer to the administration of the Gram-negative bacteria under the skin of a patient/subject. The terms "intramuscular" or "intramuscularly administered" are used interchangeably and refer to the administration of the Gram-negative bacteria into the muscle of a patient/subject. In a most preferred embodiment, the live attenuated Gram-negative bacteria is administered orally. However, it is also contemplated that other methods of administration may be used in some cases. Therefore, in certain instances the live attenuated Gram-negative bacterium of the present invention may be administered by injection, infusion, continuous infusion, intravenously, intradermally, intraarterially, intralesionally, intravaginally, intrarectally, intramuscularly, intraperitoneally, subcutaneously, subconjunctival, mucosally, intrapericardially, intraumbilically, intraocularally, intracranially, intraarticularly, intraprostaticaly, intrapleurally, intratracheally, intranasally, inhalation (e.g. aerosol inhalation), via a catheter, via a lavage, or by other method or any combination of the forgoing as would be known to one of ordinary skill in the art (see, for example, Remington's Pharmaceutical Sciences, 18th Ed. Mack Printing Company, 1990). Preferably, the Gram-negative bacterium of the present invention may be administered mucosally, intravaginally, intravenously, intranasally, intrapleurally or intradermally. In a preferred embodiment, the Gram-negative bacteria herein disclosed is not administered intratumourally.

In another embodiment of the invention, the live attenuated Gram-negative bacterium is administered to the subject in a first treatment phase and the checkpoint inhibitor therapy, adoptive T cell therapy and/or the allogeneic or autologous CAR-T therapy are administered in a second treatment phase.

By "first treatment phase" and "second treatment phase", we intend a course of treatment whereby the first treatment phase and the second treatment phase are temporally spaced, such that there is a gap between the first and second treatment phase where the patient/subject is not receiving the Gram-negative bacteria herein disclosed, or the immunotherapy herein disclosed.

Without being bound by theory, it is thought that the administration of the live attenuated Gram-negative bacterium before the immunotherapy in question (i.e. in the first treatment phase) may allow for the immune system to be effectively conditioned prior to the immunotherapy taking place, resulting in more effective targeting of the cancer or tumour upon administration of the checkpoint inhibitor therapy, adoptive cell therapy, and/or CAR T-cell therapy.

Whilst it is preferred that the live attenuated Gram-negative bacterium is administered prior to the immunotherapeutic composition, there may be some instances where it is necessary for them to be administered at the same time or after. Accordingly, the live attenuated Gram-negative bacterium and immunotherapy may be present in the same or separate pharmaceutical formulations, and administered at the same or different times.

Preferably, the first treatment phase and second treatment phase are administered at least one week apart, preferably wherein the first treatment phase and second treatment phase are administered two weeks apart.

The live attenuated Gram-negative bacterium herein disclosed may, when in use, generate a systemic immune response in the subject. Preferably, the live attenuated Gram-negative bacterium generates a systemic immune response that results in an increase in the activation and/or maturation of myeloid cells. Examples of such myeloid cells include, but are not limited to, conventional dendritic cells, plasmacytoid dendritic cells, monocytes and/or macrophages. Accordingly, a systemic immune response in the context of the present invention may refer to long-term phenotypic changes in the circulating/systemic myeloid compartment.

In a fourth aspect of the invention, there is a method of treating, inhibiting or controlling a neoplastic disease in a subject, wherein the method comprises simultaneously, separately or sequentially administering to the subject, (i) a live attenuated Gram-negative bacterium, wherein said live attenuated Gram-negative bacterium is orally administered, subcutaneously administered or intramuscularly administered and (ii) a checkpoint inhibitor therapy, an adoptive cell therapy and/or an allogeneic or an autologous CAR-T therapy, wherein said method results in an enhanced therapeutic efficacy relative to the administration of the live attenuated Gram-negative bacterium or checkpoint inhibitor therapy, an adoptive cell therapy and/or an allogeneic or an autologous CAR-T therapy alone.

In a fifth aspect of the invention, there is a method of treating, inhibiting or controlling a neoplastic disease in a subject, wherein the method comprises simultaneously, separately or sequentially administering to the subject, (i) a live attenuated Gram-negative bacterium, wherein the live attenuated Gram-negative bacterium is to be administered in a first treatment phase and (ii) a checkpoint inhibitor therapy, an adoptive cell therapy and/or an allogeneic or an autologous CAR-T therapy is to be administered in a second treatment phase, wherein said method results in an enhanced therapeutic efficacy relative to the administration of the live attenuated Gram-negative bacterium or checkpoint inhibitor therapy, an adoptive cell therapy and/or an allogeneic or an autologous CAR-T therapy alone.

In a sixth aspect of the invention, there is a method of treating, inhibiting or controlling a neoplastic disease in a subject, wherein the method comprises simultaneously, separately or sequentially administering to the subject, (i) a live attenuated Gram-negative bacterium, wherein said live attenuated Gram-negative bacterium is non-recombinant, or wherein said live attenuated Gram-negative bacterium does not comprise eukaryotic heterologous DNA encoding a therapeutic protein, and (ii) a checkpoint inhibitor therapy, an adoptive cell therapy and/or an allogeneic or an autologous CAR-T therapy, wherein said method results in an enhanced therapeutic efficacy relative to the administration of the live attenuated Gram-negative bacterium or checkpoint inhibitor therapy, an adoptive cell therapy and/or an allogeneic or an autologous CAR-T therapy alone.

Therefore, the method of the present invention may be used to reduce or inhibit metastasis of a primary tumour or cancer to other sites, or the formation or establishment of metastatic tumours or cancers at other sites distal from the primary tumour or cancer thereby inhibiting or reducing tumour or cancer relapse or tumour or cancer progression. Accordingly, the present invention provides a detectable or measurable improvement in a condition of a given subject, such as alleviating or ameliorating one or more adverse (physical) symptoms or consequences associated with the presence of a cell proliferative or cellular hyperproliferative disorder, neoplasia, tumour or cancer, or metastasis, i.e., a therapeutic benefit or a beneficial effect.

The method of the present invention is therefore a combination therapy comprising administration of a live attenuated Gram-negative bacterium and an immunotherapy, i.e. a checkpoint inhibitor therapy, an adoptive cell therapy and/or a CAR T-cell therapy, with the potential to elicit potent and durable immune responses with enhanced therapeutic benefit. The additive or synergistic nature of the herein disclosed therapeutic combination may result in lower levels of therapy or treatment being required, resulting in a reduction in adverse effects due to a more favourable toxicological profile.

A therapeutic benefit or beneficial effect is any objective or subjective, transient, temporary, or long-term improvement in the condition or pathology, or a reduction in onset, severity, duration or frequency of an adverse symptom associated with or caused by cell proliferation or a cellular hyperproliferative disorder such as a neoplasia, tumour or cancer, or metastasis. It may lead to improved survival. A satisfactory clinical endpoint of a treatment method in accordance with the invention is achieved, for example, when there is an incremental or a partial reduction in severity, duration or frequency of one or more associated pathologies, adverse symptoms or complications, or inhibition or reversal of one or more of the physiological, biochemical or cellular manifestations or characteristics of cell proliferation or a cellular hyperproliferative disorder such as a neoplasia, tumour or cancer, or metastasis. A therapeutic benefit or improvement therefore may be, but is not limited to destruction of target proliferating cells (e.g., neoplasia, tumour or cancer, or metastasis) or ablation of one or more, most or all pathologies, adverse symptoms or complications associated with or caused by cell proliferation or the cellular hyperproliferative disorder such as a neoplasia, tumour or cancer, or metastasis. However, a therapeutic benefit or improvement need not be a cure or complete destruction of all target proliferating cells (e.g., neoplasia, tumour or cancer, or metastasis) or ablation of all pathologies, adverse symptoms or complications associated with or caused by cell proliferation or the cellular hyperproliferative disorder such as a neoplasia, tumour or cancer, or metastasis. For example, partial destruction of a tumour or cancer cell mass, or a stabilization of the tumour or cancer mass, size or cell numbers by inhibiting progression or worsening of the tumour or cancer, can reduce mortality and prolong lifespan even if only for a few days, weeks or months, even though a portion or the bulk of the tumour or cancer mass, size or cells remain.

Specific non-limiting examples of therapeutic benefit include a reduction in neoplasia, tumour or cancer, or metastasis volume (size or cell mass) or numbers of cells, inhibiting or preventing an increase in neoplasia, tumour or cancer volume (e.g., stabilizing), slowing or inhibiting neoplasia, tumour or cancer progression, worsening or metastasis, or inhibiting neoplasia, tumour or cancer proliferation, growth or metastasis.

An invention method may not take effect immediately. For example, treatment may be followed by an increase in the neoplasia, tumour or cancer cell numbers or mass, but over time eventual stabilization or reduction in tumour cell mass, size or numbers of cells in a given subject may subsequently occur.

Additional adverse symptoms and complications associated with neoplasia, tumour, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of an adverse symptom or complication associated with or caused by a cellular hyperproliferative disorder, an improvement in the subjects quality of life and/or well-being, such as increased energy, appetite, psychological well-being, are all particular non-limiting examples of therapeutic benefit.

A therapeutic benefit or improvement therefore can also include a subjective improvement in the quality of life of a treated subject. In an additional embodiment, a method prolongs or extends lifespan (survival) of the subject. In a further embodiment, a method improves the quality of life of the subject.

It is envisaged that the present invention may be particularly suited to individuals who have been refractory to previous treatment with a checkpoint inhibitor, an adoptive cell therapy and/or CAR T-cell therapy. By "refractory", we intend a reference to any neoplastic disease that does not respond to treatment. It is also envisaged that the present invention will be particularly suited to individuals who have previously been low responders, moderate responders or high responders to previous immunotherapy treatment.

The live attenuated Gram-negative bacterium and immunotherapy in question will typically be administered to the subject in a composition that comprises an effective amount of the live attenuated Gram-negative bacterium or immunotherapy and further comprises a pharmaceutically acceptable carrier/adjuvant/diluent or excipient. The phrases "pharmaceutically or pharmacologically acceptable" refers to molecular entities and compositions that do not produce an adverse, allergic or other untoward reaction when administered to an animal, such as, for example, a human, as appropriate. Such preparations will be known to those skilled in the art. Moreover, for animal (e.g., human) administration, it will be understood that preparations should meet sterility, pyrogenicity, general safety and purity standards, as applicable.

As used herein, "pharmaceutically acceptable carrier/adjuvant/diluent/excipient" includes any and all solvents, dispersion media, coatings, surfactants, antioxidants, preservatives {e.g., antibacterial agents, antifungal agents), isotonic agents, absorption delaying agents, salts, preservatives, drugs, drug stabilizers, gels, binders, excipients, disintegration agents, lubricants, sweetening agents, flavouring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Examples include, but are not limited to disodium hydrogen phosphate, soya peptone, potassium dihydrogen phosphate, ammonium chloride, sodium chloride, magnesium sulphate, calcium chloride, sucrose, borate buffer, sterile saline solution (0.9% NaCl) and sterile water.

The composition, either the live attenuated Gram-negative bacterium composition or the immunotherapy, may also comprise additional components intended for enhancing an immune response. Examples of such additional components include but are not limited to; aluminium salts such as aluminium hydroxide, aluminum oxide and aluminium phosphate, oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (e.g., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), muramyldipeptides, Immune Stimulating Complexes (the "Iscoms" as disclosed in EP 109 942, EP 180 564 and EP 231 039), saponins, DEAE-dextran, neutral oils (such as miglyol), vegetable oils (such as *arachis* oil), liposomes, polyols, the Ribi adjuvant system (see, for instance, GB-A-2 189 141), vitamin E, Carbopol, interferons (e.g., IFN-alpha, IFN-gamma, or IFN-beta) or interleukins, particularly those that stimulate cell mediated immunity (e.g., IL-2, IL-3, IL-4, IL-5, IL-6, IL-7, IL-8, IL-9, IL-10, IL-11, IL-12, IL-13, IL-14, IL-15, IL-16 and IL-17).

The inventors of the present invention have surprisingly found that the combination of a live attenuated Gram-negative bacterium and an immunotherapy results in a more efficacious therapy for the prevention and/or treatment of neoplastic disease than if either component was used in isolation. The invention is further described with reference to the following non-limiting examples:

EXAMPLES

Example 1—Induction of Long-Term Phenotypic Changes in Systemic Myeloid Cells

Adult, female BALB/c mice were treated with $1 \times 10^9$ CFU *Salmonella enterica* serovar *Typhimurium* strain MD58 ($\Delta$aroC) orally. 21 days later spleens were harvested, single cell suspensions generated and flow cytometry staining performed. Median fluorescence intensity of markers CD80, CD86 and PD-L1 on viable, $CD11c^{high}$, $HLA-DR^+$, $CD11b^{+/-}$, $PDCA-1^-$ conventional dendritic cells and viable, $CD11c^{-/low}$, $PDCA1^+$, $HLA-DR^{-/int}$, $CD11b^-$ plasmacytoid dendritic cells was measured (see FIGS. 1A and 1B). Median fluorescence intensity of markers PD-L1, CD80 and HLA-DR on viable, $CD11c^-$, $CD11b^+$, $Ly6C^+$, $F4/80^-$ monocytes and viable, $CD11c^-$, $CD11b^+$, $Ly6C^-$, $F4/80^+$ macrophages was also measured (see FIGS. 1C and 1D).

As can be seen FIG. 1, various cell markers of myeloid cells, for example, conventional dendritic cells, plasmacytoid dendritic cells, monocytes and macrophages displayed a significant increase at 21 days following treatment with *Salmonella*, suggesting that the effect on activation of immune cells following treatment with *Salmonella* is sustainable over a significant period of time.

Example 2—Time-Course of *Salmonella*-Induced Phenotypic Changes

To explore the kinetics of activation/maturation phenotypic changes on myeloid cells observed in FIG. 1, we performed a time-course study. Adult, female BALB/c mice were treated with $1 \times 10^9$ CFU *Salmonella enterica* serovar *Typhimurium* strain MD58 ($\Delta$aroC) orally. 1, 14, 21 or 42 days later spleens and femurs were harvested, single cell suspensions generated and flow cytometry staining performed (see experiment schematic of FIG. 2A).

Figure 2B:
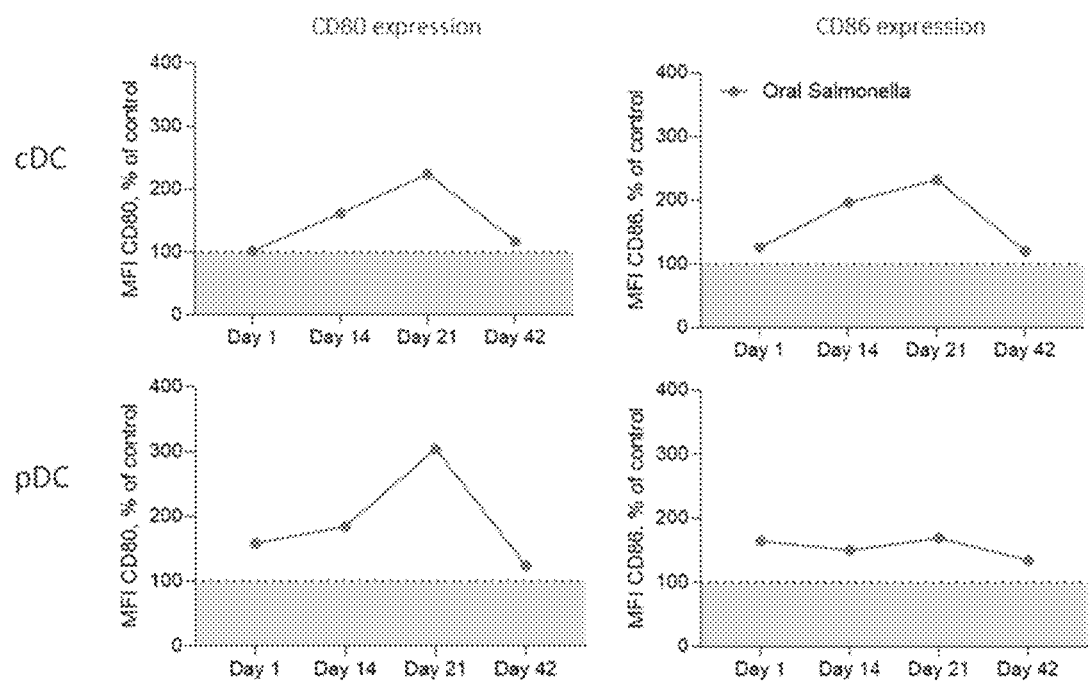
Figure 2C:
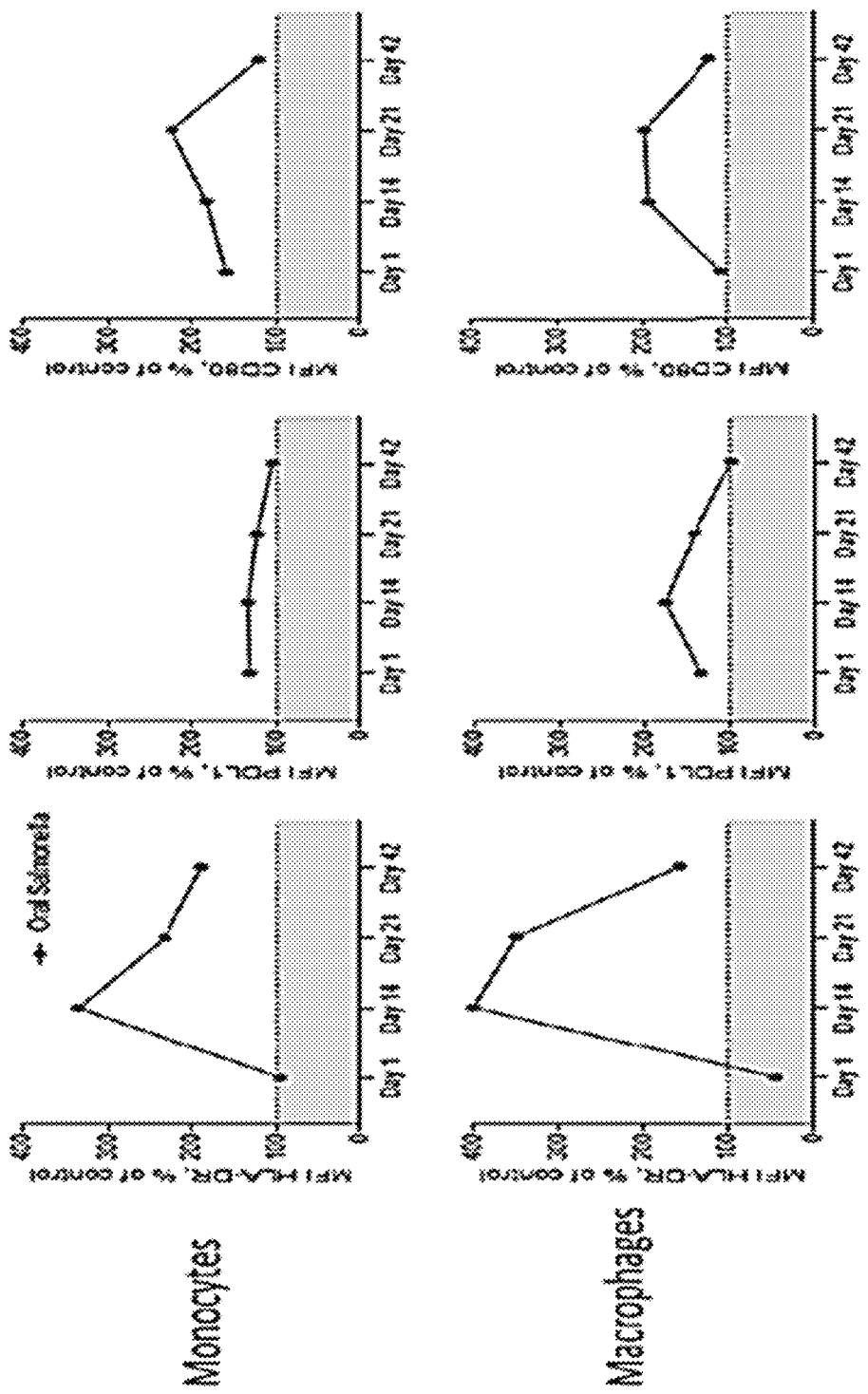

Activation markers on systemic conventional (cDC) and plasmacytoid (pDC) dendritic cells were shown to be up-regulated following oral administration of *Salmonella*, peaking at 3 weeks post-administration and returning close to baseline levels by 6 weeks post-administration (see FIG. 2B). Activation markers on systemic monocytes and macrophages were also shown to be up-regulated following oral administration of *Salmonella*, peaking at 3 weeks post-administration and returning close to baseline levels by 6 weeks post-administration (see FIG. 2C).

Example 3—Oral Administration of *Salmonella* Enhances Myelopoiesis

Adult, female BALB/c mice were treated with $1 \times 10^9$ CFU *Salmonella enterica* serovar *Typhimurium* strain MD58 ($\Delta$aroC) orally. 1, 14, 21 or 42 days later flow cytometry staining of isolated bone marrow cells was performed.

Figure 3A:
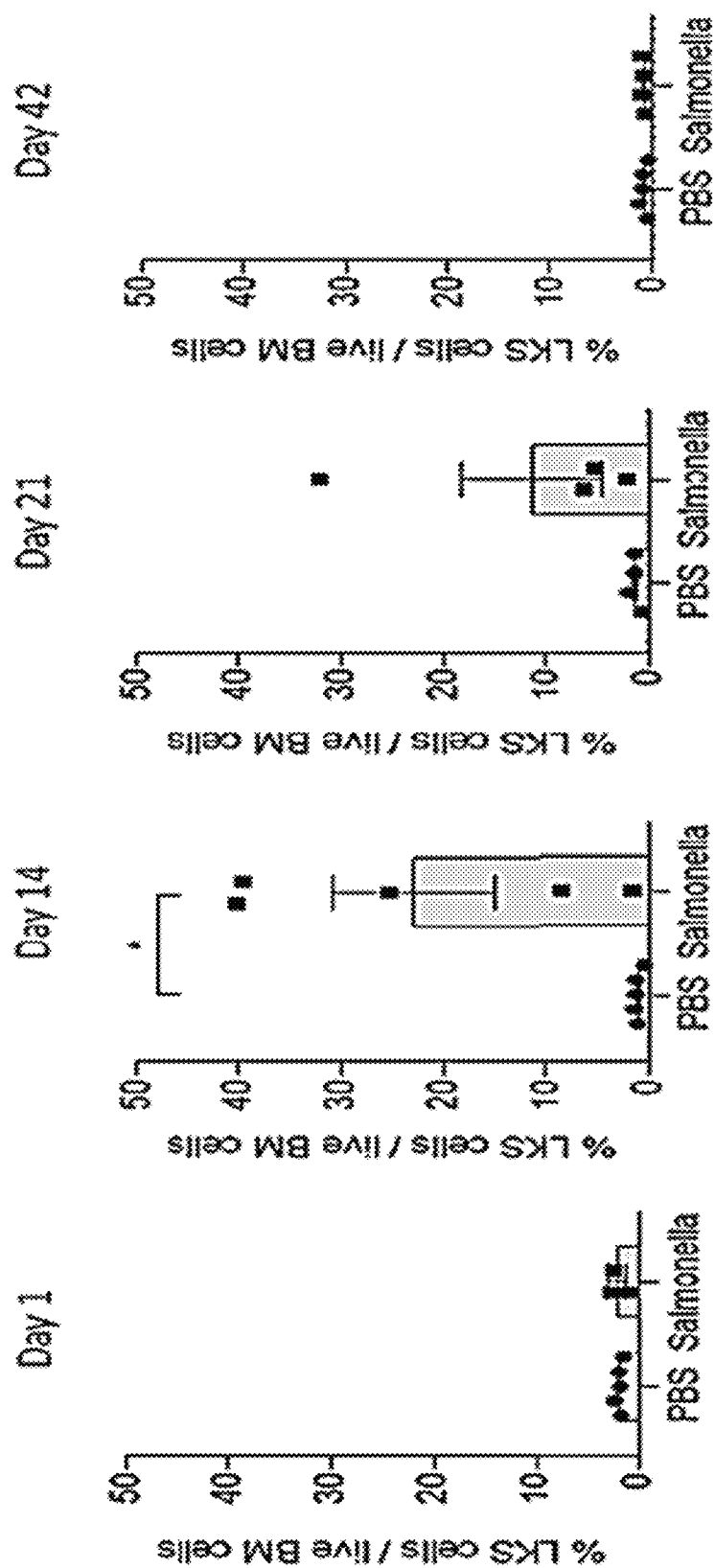
FIG. 3A-C shows oral administration of *Salmonella* results in enhanced myelopoiesis. A) Graphs show the % of lineage negative ($CD5^-$, $CD11b^-$, $B220^-$, $GR-1^-$, $Terr-119^-$, $Ly-6B.2^-$) viable cells expressing both c-Kit and Sca-1, termed LKS cells of total bone marrow cells. n=4-5 mice/group; B) Representative flow cytometry plots showing increase in viable LKS cells in the bone marrow of animals treated orally with *Salmonella*; C) % viable LKS cells of total bone marrow cells at day 14 after *Salmonella* treatment was correlated with % monocytes (viable, $CD11c-$, $CD11b+$, $Ly6C+$, $F4/80-$ cells) at the same timepoint using Spearman rank correlation.
Figure 3B:
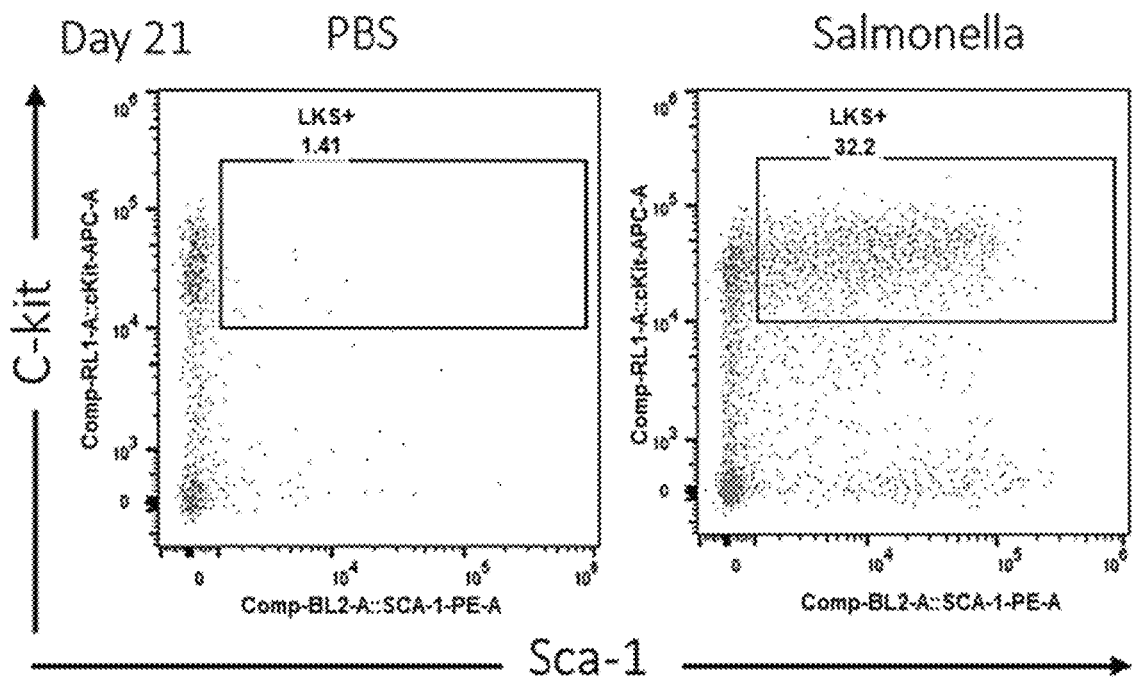
Figure 3C:
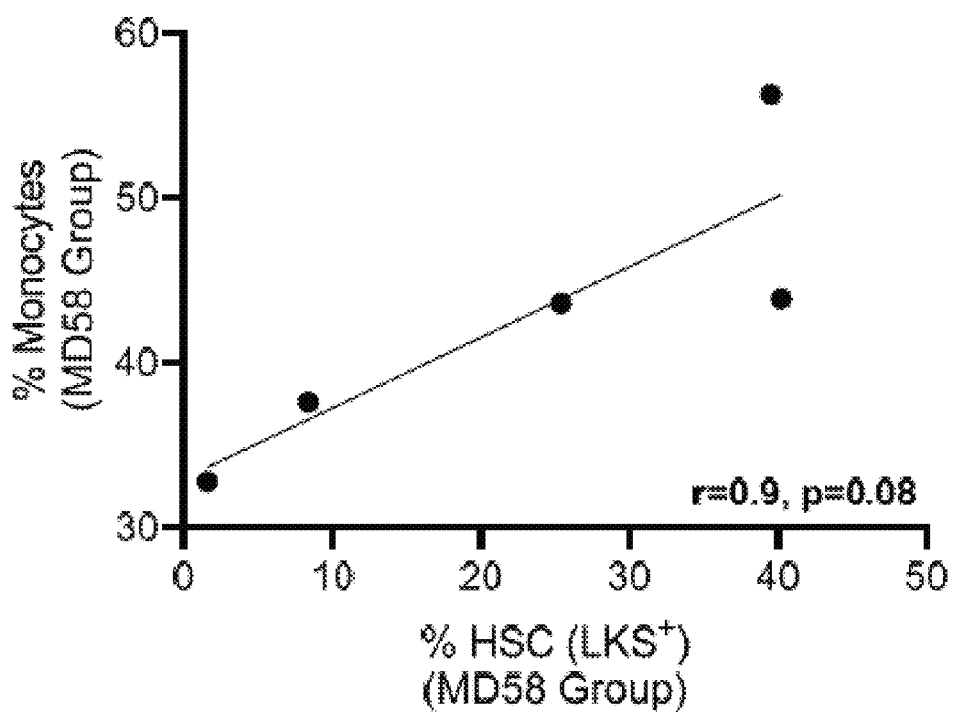

The number of hematopoietic stem cells/multipotent progenitors in the bone marrow is shown to increase significantly 2 weeks after oral administration (see FIG. 3A). Representative flow cytometry plots also demonstrate an increase in viable LKS cells in the bone marrow of animals treated orally with *Salmonella* (see FIG. 3B). Additionally, the % of viable LKS cells of total bone marrow cells at day 14 after *Salmonella* treatment was correlated with % monocytes (viable, $CD11c^-$, $CD11b^+$, $Ly6C^+$, $F4/80^-$ cells) at the same timepoint using Spearman rank correlation (see FIG. 3C).

Accordingly, the data herein supports the hypothesis that administration of *Salmonella* conditions the immune system, and in particular the myeloid arm of the immune system. Furthermore, these data demonstrate long-term effects of *Salmonella* conditioning on the immune system, as demonstrated by the 3-6 weeks duration of conditioning changes induced by *Salmonella*. These changes are likely systemically/centrally mediated, as suggested by the positive correlation between the number of bone marrow hematopoietic progenitor cells and splenic monocytes.

Example 4-Oral Administration of *Salmonella* Induces a Hyperresponsive State in Systemic Dendritic Cells Lasting at Least 14 Days Adult, female BALB/c mice were treated with $1 \times 10^9$ CFU *Salmonella enterica* serovar *Typhimurium* strain MD58 ($\Delta$aroC) orally. 14 days later spleens were harvested, single cell suspensions generated, CD11c expressing cells were enriched by magnetic separation and $1 \times 10^5$ cells/well were incubated with the indicated stimuli (TLR9, TLR2/6, or TLR4/2 agonists or a control) for 24 hrs. IL-6 in the supernatant was measured by LegendPlex assay (see FIG. 4).

Figure 4:
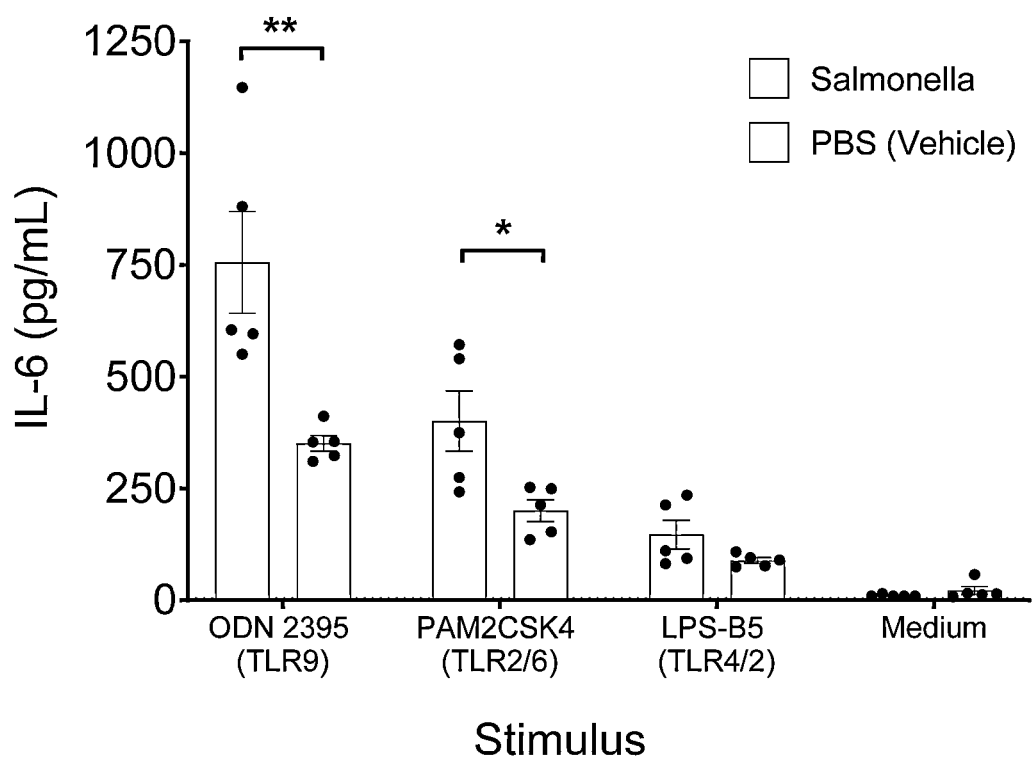
FIG. 4 shows orally administered *Salmonella* induces a hyperresponsive state in systemic dendritic cells that lasts at least 14 days. n=5 mice per group from a single study; bars are mean+/–SEM; Statistics indicated are Mann-Whitney test.

As is evident from FIG. 4, CD11c expressing cells from animals that had been treated with a Gram-negative bacteria, for example, *Salmonella*, demonstrated enhanced IL-6 secretion (an indicator of the level of immune responsiveness of a cell) in response to a variety of stimuli when compared to the vehicle control group. This further supports that the administration of Gram-negative bacteria of the present invention results in conditioning of immune cells, rendering them more responsive to subsequent stimuli.

As demonstrated in Examples 1 to 4, the experimental data herein disclosed shows that treatment with a live attenuated Gram-negative bacterium, for example, *Salmonella*, results in an unexpected long-term activation of multiple immune cell types (e.g. dendritic cells, monocytes and macrophages), as well as an increase in hematopoietic stem cells/multipotent progenitors in the bone marrow. Without being bound by theory, it is believed that the systemic response induced by administration of such a live attenuated Gram-negative bacterium is able to condition the immune system of a subject or patient such that when administered in combination with an immunotherapy, for example, a checkpoint inhibitor therapy, adoptive cell therapy or CAR T-cell therapy, the anti-tumour activity of such immunotherapies is enhanced. This is further demonstrated in Example 5 below. It is believed that the systemic modifications observed from administering the live attenuated Gram-negative bacteria, i.e., the activation of multiple immune cell types and effect on myelopoiesis (as demonstrated herein), in combination with the intestinal uptake of said live attenuated Gram-negative bacteria is responsible for the enhanced anti-tumour effect observed. The skilled person will readily understand that the broad systemic effects induced by the live attenuated Gram-negative bacterium may condition the immune system of a patient/subject in such a way that the advantageous effects are observed across a myriad of checkpoint inhibitors and/or adoptive cell therapies, i.e. they are not restricted to a single therapy but are applicable across the class of therapies. Additionally, the use of Gram-negative bacteria to condition the immune system of a subject/patient may be particular advantageous for those patients/subjects who have been shown to be resistant to immunotherapies when used in isolation.

Example 5—Treatment with Orally Administered *Salmonella* Results in Slower Tumour Growth and in Enhanced Efficacy when Given in Combination with Immune Checkpoint Inhibitors Adult, female C57BL/6 mice were inoculated subcutaneously with $1 \times 10^6$ MC38 (colon cancer) or B16-F10 (melanoma) tumour cells.

Figure 5A:
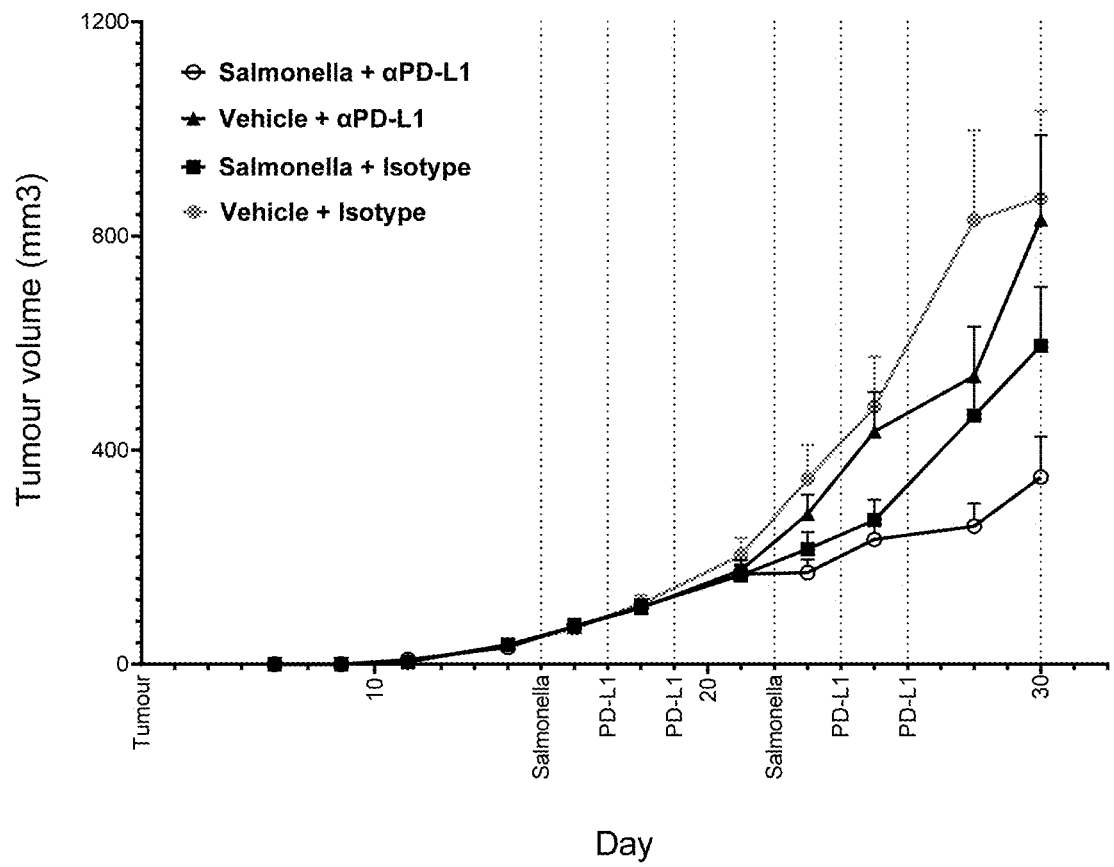
FIG. 5A-B shows treatment with orally administered *Salmonella* results in slower tumour growth and in enhanced efficacy when given in combination with immune checkpoint inhibitors. A) Graph shows MC38 tumour volume over time, depicting tumour growth. Table summarizes the average % tumour growth inhibition between days 14 and 30 of different treatments relative to the control group (Vehicle+Isotype). Data are mean+/–SEM of 10 mice per group. B) Graph shows tumour volume over time, depicting tumour growth. Table summarizes the average % tumour growth inhibition between days 16 and 18 of different treatments relative to the control group (Vehicle+Isotype). Data are mean+/–SEM of 9-10 mice per group.

For FIG. 5A, MC38 tumour bearing animals were treated orally with $1 \times 10^9$ CFU *Salmonella enterica* serovar *Typhimurium* strain MD58 ($\Delta$aroC), or PBS control, 15 and 22 days after tumour inoculation, and with 10 mg/kg anti-PD-L1 twice weekly from day 17. Graph shows tumour volume over time, depicting tumour growth and the corresponding table summarizes the average % tumour growth inhibition following treatment with *Salmonella* and isotype control, *Salmonella* and αPD-L1, or the vehicle and αPD-L1 between days 14 and 30 relative to the control vehicle and isotype group (see FIG. 5A).

Figure 5B:
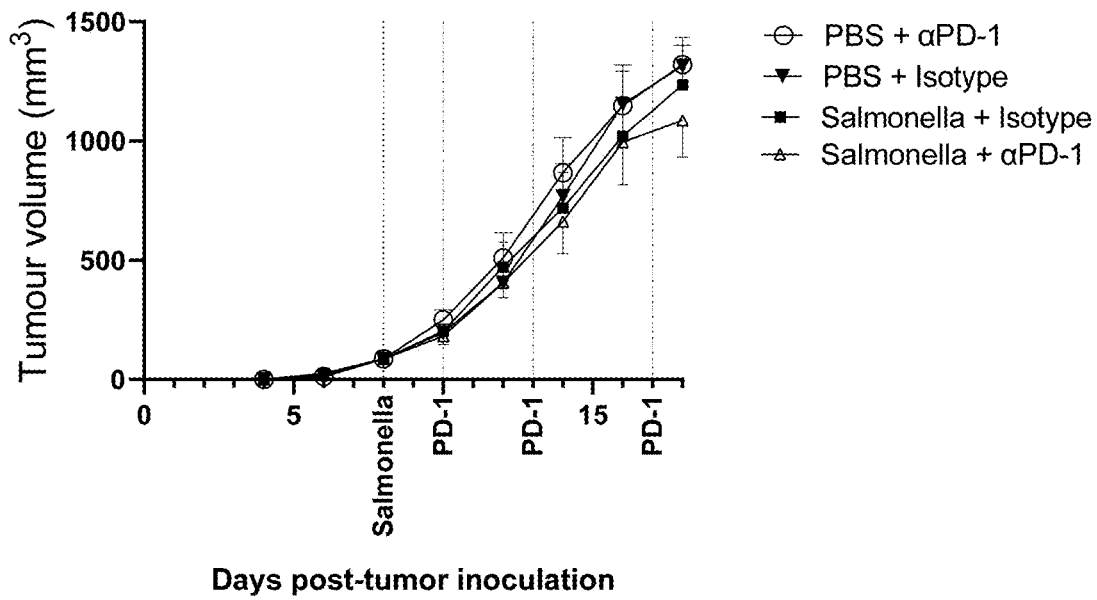

For FIG. 5B, B16-F10 tumour bearing animals were treated orally with $1 \times 10^9$ CFU *Salmonella enterica* serovar *Typhimurium* strain MD58 ($\Delta$aroC), or PBS control, on day 8 post tumour-inoculation, and with 10 mg/kg anti-PD-1 antibody on days 10, 13 and 17. Graph shows tumour volume over time, depicting tumour growth and the corresponding table summarizes the average % tumour growth inhibition between days 14 and 30 of different treatments relative to the control group (Vehicle+Isotype) (see FIG. 5B).

As discussed above, it is known that whilst immunotherapies such as checkpoint inhibitor therapies, adoptive cell therapies and CAR-T therapies have been successful in a sub-population of patients, there remains a large proportion of patients for which these therapies have little to no effect. As such, it is of paramount importance to find therapies in the oncology field that address this unmet need. This issue is reflected in the Tables presented in FIGS. 5A and 5B, wherein treatment with a checkpoint inhibitor is shown to have no effect or minimal effect on tumour growth inhibition, but not an effect that is shown to be significantly better than that produced by the vehicle and isotype control. However, in stark contrast, when the checkpoint inhibitor is given in combination with a live attenuated Gram-negative bacteria, for example, *Salmonella*, the % of tumour growth inhibition is significantly improved (approximately 13× the growth inhibition seen with the checkpoint inhibitor alone group in FIG. 5A). This effect is also significantly higher than that seen with treatment of the *Salmonella* alone, highlighting the advantages of using the two components in combination. Accordingly, the inventors of the present invention have surprisingly shown that the anti-tumour efficacy of immunotherapies, such as checkpoint inhibitors, adoptive cell therapies and CAR-T therapies, can be significantly enhanced when given in combination with a live attenuated Gram-negative bacteria.

Additionally, the inventors have demonstrated the same trend of an additive and/or synergistic effect in two unrelated tumour models and with two different checkpoint inhibitors, underpinning and supporting the hypothesis that the conditioning effects induced by the live attenuated Gram-negative bacterium will condition the immune system of a patient/subject in such a way that the advantageous effects are observed across a myriad of checkpoint inhibitors and/or adoptive cell therapies, as well as potentially beneficial across a number of cancer indications. Accordingly, the skilled person will readily understand that the effect of the invention is agnostic to tumour type.

Example 6—In Vitro Conditioning of Macrophages with *Salmonella* Further Polarizes M1 Cells into an Inflammatory Phenotype and Induces M2 to M1-Like Phenotype Macrophages It is widely accepted that macrophages can be typically divided into M1 macrophages (proinflammatory, classically activated) and M2 macrophages (anti-inflammatory, alternatively activated/suppressive) based on their phenotype and functionality. Macrophages have previously been shown to be involved, either directly or indirectly, in several key features of malignant tumours, including angiogenesis, invasiveness, metastasis, regulation of the tumour microenvironment, and therapeutic resistance. However, they also have the capability to present tumour antigens, support tumour-specific T cell proliferation and expansion, phagocytose cancerous cells and remodel the tumour environment in such a way that the tumour becomes more susceptible to therapeutics. It is also known that the repolarization of M2 to M1 phenotype macrophages is sufficient to cause an anti-cancer effect (Duan and Luo, Targeting macrophages in cancer immunotherapy, *Signal Transduction and Targeted Therapy*, 2021(6:127)). Accordingly, treatment strategies that can initiate such a repolarisation effect would be particularly advantageous to help support and reinforce an anti-tumour effect of other immunotherapies, such as adoptive cell therapies and checkpoint inhibitors.

Figure 6:
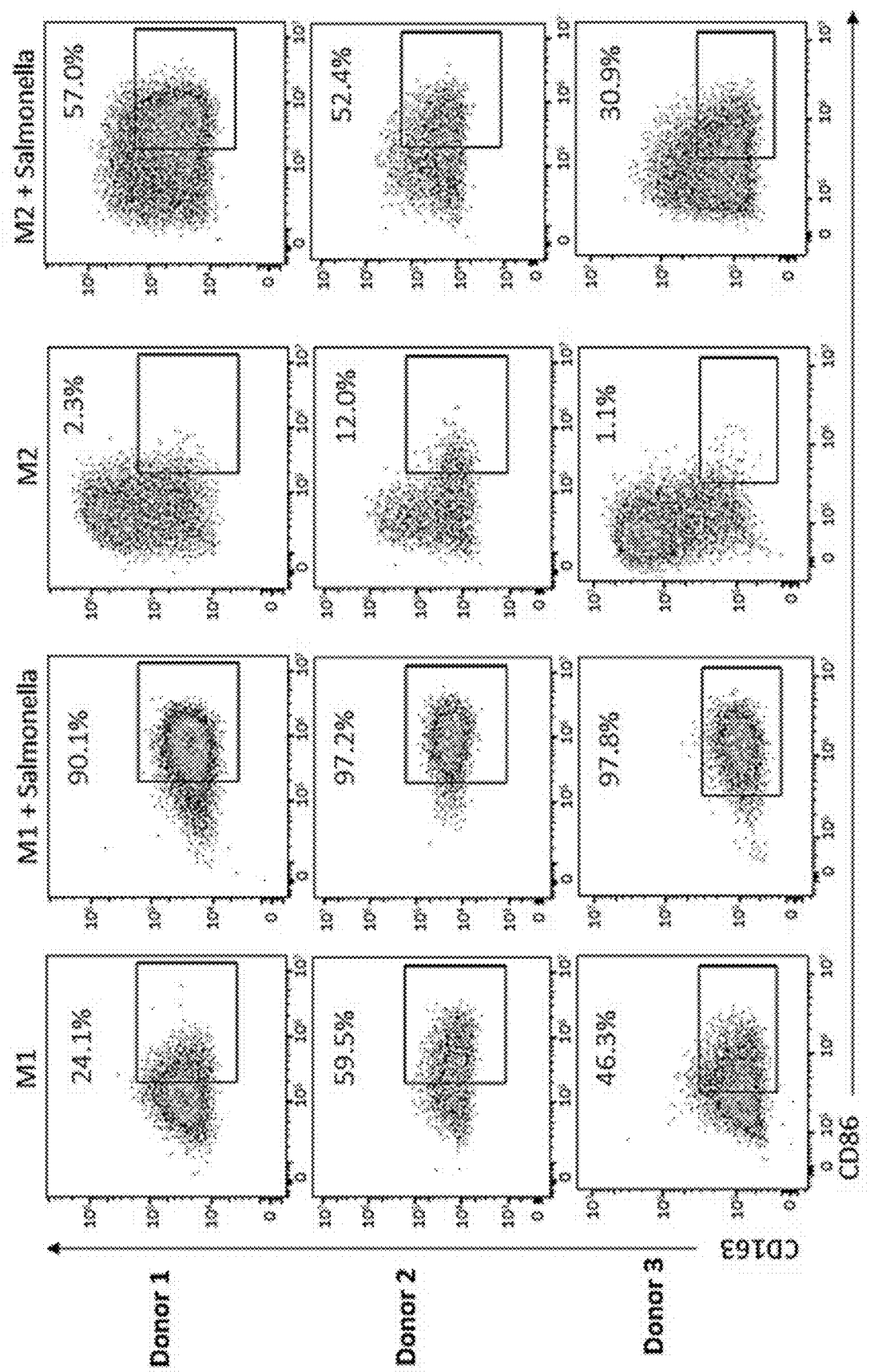
FIG. 6 shows in vitro conditioning of macrophages with *Salmonella* further polarizes M1 cells into an inflammatory phenotype and induces M2 to M1-like phenotype macrophages. Data represent monocyte-derived macrophages from 3 independent donors.

As shown herein, treatment of M2 macrophages in vitro with a Gram-negative bacteria not only results in the activation of a range of immune cells and myelopoiesis (see Examples 1 to 4), but also initiates a phenotypic switch in suppressive M2 macrophages to a M1-like phenotype (see FIG. 6). Without being bound by theory, it is thought that such a repolarization of M2 macrophages to M1 macrophages further contributes to the anti-tumour effect herein demonstrated.

PBMCs from 3 independent donors were isolated by Ficoll-Paque gradient centrifugation from Buffy Coats. CD14$^+$ monocytes were isolated using a CD14 MicroBeads isolation kit (MiltenyiBiotec) and cultured for 6 days with GM-CSF for M1 cells and with M-CSF for M2 cells. Cytokine cocktails were added on day 8 to polarize cells towards M1 and M2 cells. Resultant macrophages were harvested, washed and treated with *Salmonella enterica Typhi* strain ZH9 (ΔaroC, ΔssaV) at MOI of 1 or were left untreated. After 1 h, cells were harvested, washed and cultured in media for 48 h. They were then stained with antibodies against CD163 and CD86 prior to flow cytometry analysis.

The results presented in FIG. 6 show that *Salmonella* has an effect on both M1 and M2 macrophages. When M1 macrophages are conditioned with *Salmonella*, virtually all cells express CD86 and downregulate CD163, combination of features characteristic of pro-inflammatory anti-tumour macrophages. Likewise, this same CD86$^+$ CD163$^-$ population which is absent/low in M2 suppressive macrophages, appears in this cell population following conditioning with *Salmonella*. This suggests that suppressive M2 macrophages that are commonly associated with the tumour microenvironment (often referred to as TAM—tumour-associated macrophages) and poor prognosis can be changed by *Salmonella* conditioning towards a more pro-inflammatory phenotype likely to better support anti-tumour responses.

Example 7—In Vitro Conditioning of Human Monocytes Overcomes M2 Polarization and Reduces their Suppressive Capacity M2-like macrophages, for example, tumour-associated macrophages, are known to have an immunosuppressive effect on a variety of immune cell types via several mechanisms, including T cells (Quaranta and Schmid, Macrophage-Mediated Subversion of Anti-Tumour Immunity, *Cells*, 2019 (8(7):747). With their known ability for antigen-directed cytotoxicity, T cells are a key target in the development of various immunotherapies. Accordingly, the effect on T cell proliferation following in vitro conditioning of human monocytes with a Gram-negative bacteria was investigated.

PBMCs were isolated by Ficoll-Paque gradient centrifugation from Buffy Coats and CD14$^+$ monocytes were isolated using a CD14 MicroBeads isolation kit (MiltenyiBiotec). Monocytes were treated with *Salmonella enterica Typhi* strain ZH9 (ΔaroC, ΔssaV) for 30 minutes at MOI 1 (conditioned cells) or incubated with media only (non-conditioned cells). Cells were washed twice with PBS to remove *Salmonella* and cultured for 6 days with gentamycin supplemented media. IL-4, IL-10 and TGFβ were then added for 48 h in order to polarize cells into immunosuppressive macrophages. Autologous CD4$^+$ T cells were isolated and labeled with CellTrace Far Red. T cells were then co-cultured with the macrophages in the presence of anti CD3/CD28 Abs. After 5 days, cells were harvested, and T cell proliferation assessed using flow cytometry.

Figure 7A:
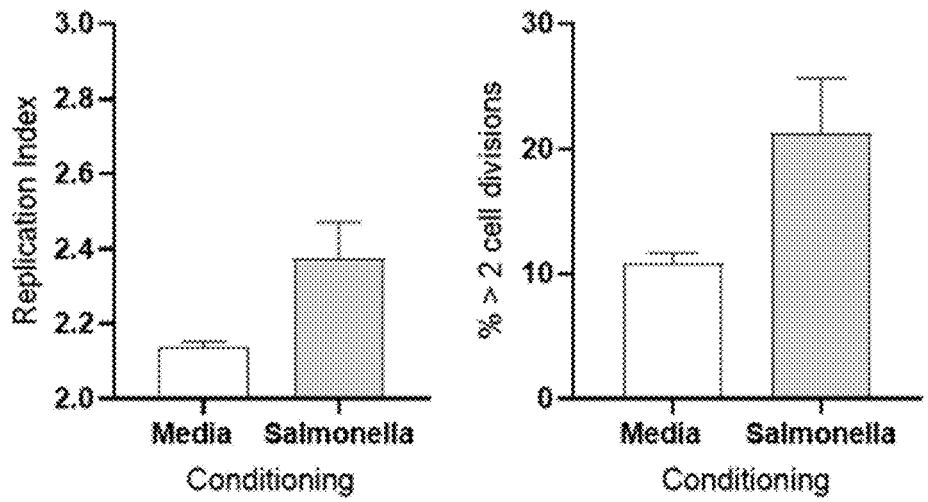
FIG. 7A-C shows in vitro conditioning of human monocytes overcomes M2 polarization and reduces their suppressive capacity. A) Graphs represent the Replication Index showing the fold-expansion of responding T cells and percentage of T cells that underwent more than 2 cells divisions; B) Positive control data demonstrating the effective stimulation of T cells by anti-CD3/28 antibodies; C) Representative flow cytometry plots showing increase in T cell proliferation in the presence of *Salmonella*-conditioned monocyte-derived macrophages.
Figure 7B:
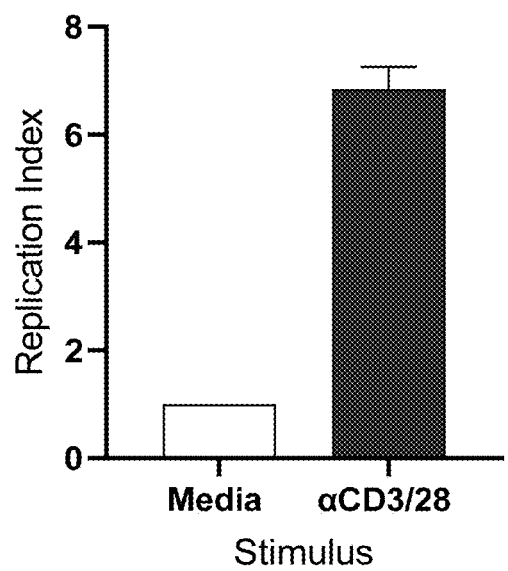
Figure 7C:
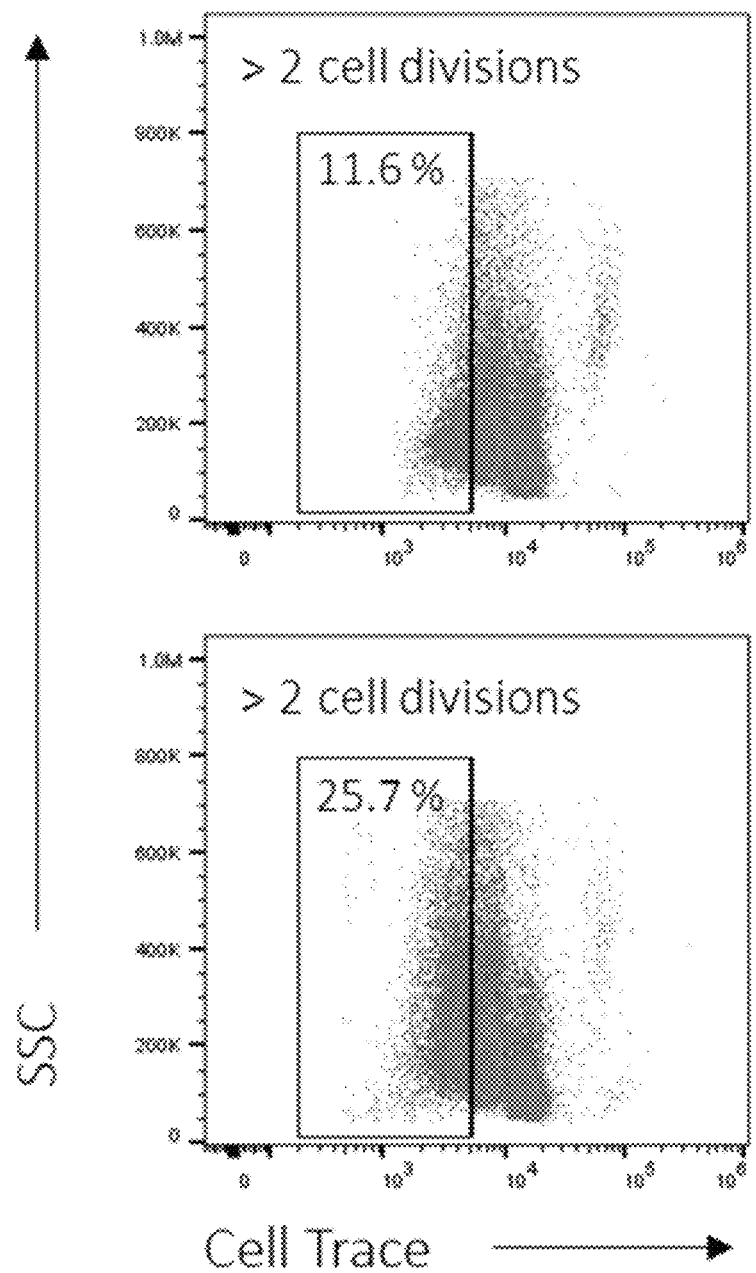

*Salmonella*-conditioned human monocyte-derived M2 macrophages were shown to be less suppressive of T cell proliferation, as demonstrated by greater T cell proliferation in the presence of *Salmonella*-conditioned macrophages compared to non-conditioned macrophages (see FIGS. 7A and 7C). As can be seen from FIG. 7C, non-conditioned (media) myeloid cells behave as suppressive M2 cells, effectively suppressing T cell proliferation, with only an average 10% of activated T cells undergoing more than 2 divisions. In contrast, *Salmonella* conditioned myeloid cells are less suppressive with an average 20% of T cells undergoing more than 2 divisions. Thus, *Salmonella*-conditioned monocyte-derived macrophages are less susceptible to M2 polarization.

These data suggest that conditioning of myeloid cells with a Gram-negative bacteria can enhance T cell proliferation in suppressive conditions, such as the tumour microenvironment, and support the hypothesis that conditioning by oral administration of a Gram-negative bacteria will enhance the proliferation of adoptively transferred and CAR T-cell therapies.

Example 8—In Vitro Training of Human Monocytes Overcomes M2 Polarization and Enhances Anti-PD-L1 Ab Activity Following the observation that conditioning myeloid cells with a Gram-negative bacteria can enhance T cell proliferation in suppressive conditions, it was subsequently explored whether such an effect had an impact on immunotherapy efficacy.

PBMCs were isolated by Ficoll-Paque gradient centrifugation from Buffy Coats and CD14$^+$ monocytes were isolated using a CD14 MicroBeads isolation kit (MiltenyiBiotec). Monocytes were treated with *Salmonella enterica Typhi* strain ZH9 (ΔaroC, ΔssaV) for 30 minutes at MOI 1 (conditioned cells) or in media only (non-conditioned cells). Cells were washed twice with PBS to remove *Salmonella* and cultured for 6 days with gentamycin supplemented media. IL-4, IL-10 and TGFβ were then added for 48 h in order to polarize cells into immunosuppressive M2 macrophages. Autologous CD4$^+$ T cells were isolated and labeled with CellTrace Far Red. Cells were then co-cultured with the macrophages in the presence of anti CD3/CD28 Abs and either anti-PD-L1 Ab or associated Isotype Ab control. After 5 days, cells were harvested, and T cell proliferation assessed using flow cytometry.

Figure 8A:
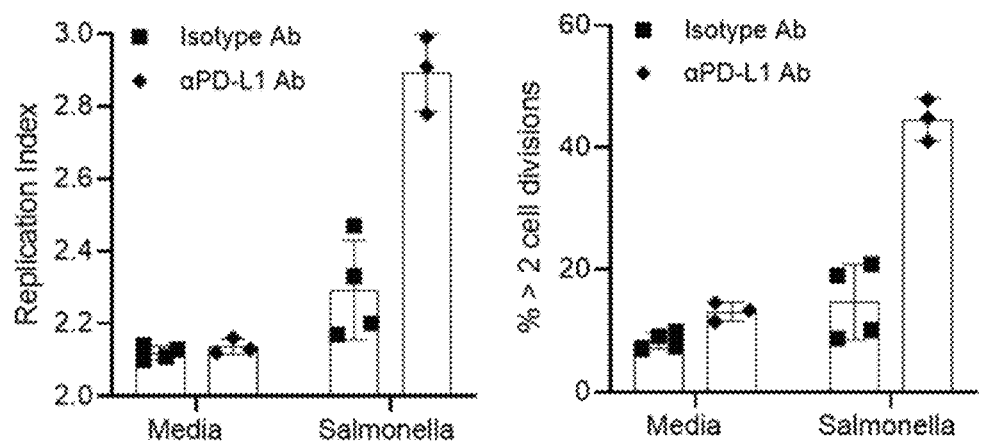
FIG. 8A-C shows in vitro conditioning of human monocytes overcomes M2 polarization and enhances anti-PD-L1 Ab activity. *Salmonella*-conditioned human monocyte-derived macrophages enhance PD-L1 blockade efficacy. A) Graphs show Replication Index representing the fold-expansion of responding T cells and percentage of T cells that underwent more than 2 cells divisions; B) Positive control data demonstrating the effective stimulation of T cells by anti-CD3/28 antibodies; C) Representative flow cytometry plots of CellTrace dilution showing the increase in T cell proliferation when PD-L1 blockade and *Salmonella*-conditioned monocyte-derived macrophages are combined.
Figure 8B:
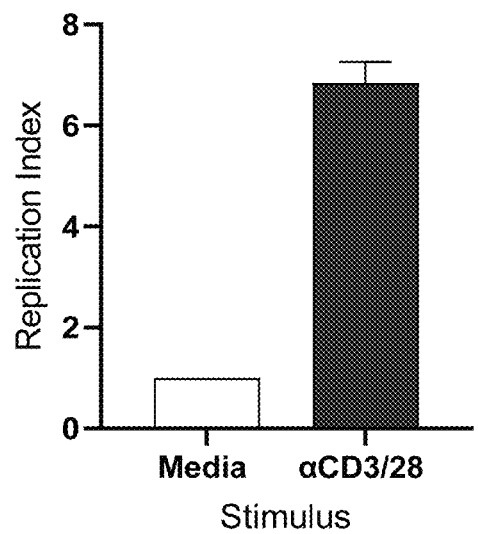
Figure 8C:
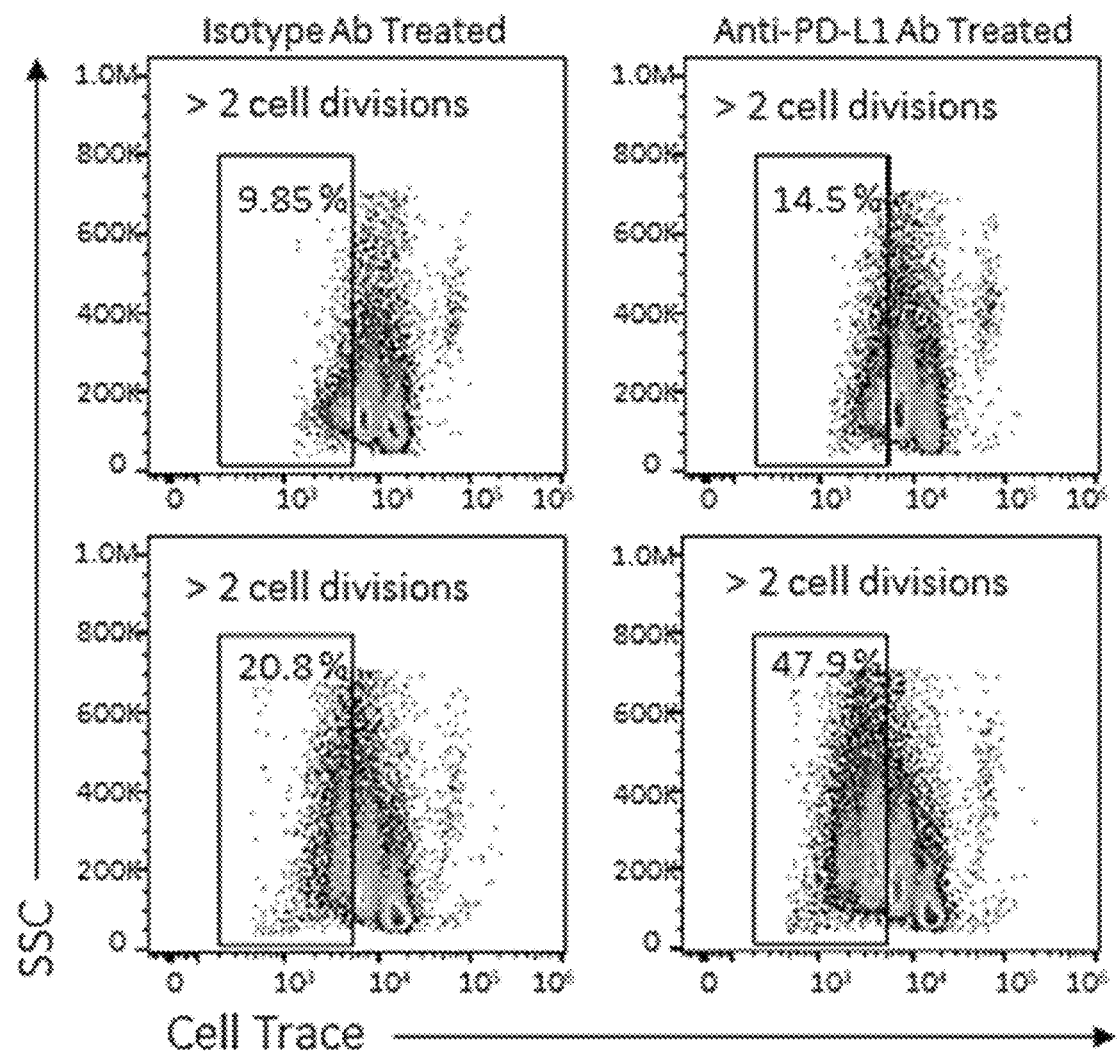

*Salmonella*-conditioned human monocyte-derived macrophages were shown to enhance PD-L1 blockade efficacy compared to those that had not been exposed to *Salmonella* (see FIGS. 8A and C). As can be seen from FIG. 8C, non-conditioned (media) myeloid cells in combination with PD-L1 blockade are not effective at reversing the suppression of T cell proliferation in this experimental setting mimicking the tumour microenvironment. However, *Salmonella* conditioned myeloid cells in combination with PD-L1 blockade render the suppression checkpoint-sensitive, reversing the suppression of T cell proliferation in the presence of PD-L1 blockade, with ~50% of cells undergoing more than 2 divisions.

These data show that conditioning of myeloid cells with a Gram-negative bacteria enables and enhances the efficacy of checkpoint blockade to revert the suppression of T cell proliferation in strongly immuno-suppressive conditions, such as the tumour microenvironment in patients who are not responsive to checkpoint inhibition therapy. Thus, the data supports the hypothesis that conditioning by administration of a Gram-negative bacteria will enhance the efficacy of immunotherapies, such as checkpoint inhibitors, adoptive cell therapies and CAR-T therapies.

Accordingly, the inventors of the present invention have demonstrated across a number of assays, both in rodent and human cells, that the use of a Gram-negative bacterium in combination with an immunotherapy, for example, a checkpoint inhibitor therapy, an adoptive cell therapy and/or an allogeneic or an autologous CAR-T therapy can enhance the anti-tumour efficacy of said therapies when compared to using the immunotherapy alone. Thus, the present invention represents a significant step forward in the field of oncology and at the very least offers a novel treatment strategy for those patients who are currently, for unknown reasons, unresponsive to current immunotherapies being used in the clinic.

The invention claimed is:

1. A method of treating, reducing, inhibiting or controlling a neoplastic disease in a subject undergoing or intended to undergo a checkpoint inhibitor therapy, an adoptive cell therapy and/or an allogenic or autologous CAR-T therapy, comprising administering simultaneously, separately or sequentially a live attenuated Gram-negative bacterium, wherein the live attenuated Gram-negative bacterium is orally administered, subcutaneously administered, intradermally administered or intramuscularly administered, wherein said live attenuated Gram-negative bacterium is non-recombinant or does not comprise eukaryotic heterologous DNA encoding a therapeutic protein.

2. The method of claim 1, wherein the live attenuated Gram-negative bacterium is to be administered in a first treatment phase and the checkpoint inhibitor therapy, the adoptive T cell therapy or the allogeneic or the autologous CAR-T therapy is to be administered in a second treatment phase.

3. The method of claim 1, wherein the live attenuated Gram-negative bacterium is a *Salmonella* spp.

4. The method of claim 1, wherein the live attenuated Gram-negative bacterium is *Salmonella enterica*.

5. The method of claim 1, wherein the live attenuated Gram-negative bacterium is *Salmonella enterica* serovar *Typhi* or wherein the live attenuated Gram-negative bacterium is *Salmonella enterica* serovar *Typhimurium*.

6. The method of claim 1, wherein the live attenuated Gram-negative bacterium is a genetically engineered non-natural bacterium.

7. The method of claim 1, wherein the live attenuated Gram-negative bacterium is selected from the group consisting of Ty21a, CVD 908-htrA, CVD 909, Ty800, M01ZH09, x9633, x9640, x8444, DTY88, ZH9PA, MD58, WT05, ZH26, SL7838, SL7207, VNP20009 and A1-R.

8. The method of claim 1, wherein the checkpoint inhibitor is a blocking agent directed against CTLA-4, PD-1, PD-L1, LAG-3, TIM-3, BTLA, TIGIT, VISTA or any combinations thereof.

9. The method of claim 8, wherein the checkpoint inhibitor is a blocking agent directed against CTLA-4, PD-1 or PD-L1.

10. The method of claim 1, wherein the adoptive cell therapy is a tumour-infiltrating lymphocyte (TIL) therapy, engineered T-cell receptor (TCR) therapy and/or natural killer (NK) cell therapy.

11. The method of claim 1, wherein the neoplastic disease is associated with a solid tumour or haematological malignancy.

12. The method of claim 1, wherein the neoplastic disease is associated with a cancer selected from prostate cancer, liver cancer, renal cancer, lung cancer, breast cancer, colorectal cancer, bladder cancer, pancreatic cancer, brain cancer, hepatocellular carcinoma, lymphoma, leukaemia, gastric cancer, cervical cancer, ovarian cancer, thyroid cancer, melanoma, carcinoma, head and neck cancer, skin cancer or sarcoma.

13. The method of claim 12, wherein the neoplastic disease is associated with a cancer selected from lung cancer, bladder cancer, gastric cancer, ovarian cancer, colorectal cancer, head and neck cancer, melanoma, renal cancer or breast cancer.

14. The method of claim 1, wherein the live attenuated Gram-negative bacterium is orally administered.

15. The method of claim 1, wherein the live attenuated Gram-negative bacterium is administered in a first treatment phase and the checkpoint inhibitor therapy, adoptive T cell therapy and/or the allogeneic or autologous CAR-T therapy are administered in a second treatment phase.

16. The method of claim 2, wherein the first treatment phase and second treatment phase are administered at least one week apart.

17. The method of claim 2, wherein the first treatment phase and second treatment phase are administered two weeks apart.

18. The method of claim 1, wherein said live attenuated Gram-negative bacterium generates a systemic immune response in the subject.

19. The method of claim 18, wherein the systemic immune response results in an increase in the activation and/or maturation of myeloid cells.

20. The method of claim 11, wherein the neoplastic disease is associated with a solid tumour.

* * * * *